(12) United States Patent
Sanders, Jr.

(10) Patent No.: US 12,042,181 B2
(45) Date of Patent: Jul. 23, 2024

(54) SURGICAL PIN COMPRESSABLE WOUND DRESSING MODULE, DEVICE, AND SYSTEM

(71) Applicant: Stephen Michael Sanders, Jr., Port S. Lucie, FL (US)

(72) Inventor: Stephen Michael Sanders, Jr., Port S. Lucie, FL (US)

( * ) Notice: Subject to any disclaimer, the term of this patent is extended or adjusted under 35 U.S.C. 154(b) by 186 days.

(21) Appl. No.: 16/741,916

(22) Filed: Jan. 14, 2020

(65) Prior Publication Data

US 2020/0155198 A1 May 21, 2020

Related U.S. Application Data

(63) Continuation-in-part of application No. 15/646,930, filed on Jul. 11, 2017, now Pat. No. 10,695,237.

(Continued)

(51) Int. Cl.
*A61F 15/00* (2006.01)
*A61B 17/64* (2006.01)
*A61F 13/00* (2024.01)

(52) U.S. Cl.
CPC .......... *A61B 17/6416* (2013.01); *A61F 13/00* (2013.01); *A61F 2013/0028* (2013.01)

(58) Field of Classification Search
CPC ....... A61B 17/685; A61B 17/60; A61B 17/66; A61B 17/864; A61B 17/8685; A61B 17/64; A61B 17/6425; A61B 17/6433; A61B 17/6441; A61B 17/645; A61B 17/6458; A61B 17/08; A61B 17/7001; A61B 2017/00544; A61B 17/155; A61B 17/157; A61B 2090/365; A61B 2017/00216; A61B 17/1666; A61B 90/37; A61B 2034/104; A61B 2017/568; A61B 2090/368; A61B 2090/37336; A61B 17/17; A61B 17/1742; A61B 2034/2059; A61B 34/74; A61B 2034/105; A61B 2034/108;

(Continued)

(56) References Cited

U.S. PATENT DOCUMENTS 4,856,504 A * 8/1989 Yamamoto ........ A61F 13/49009
606/59
4,915,694 A * 4/1990 Yamamoto ............ A61M 25/02
604/180

(Continued)

*Primary Examiner* — Kim M Lewis
(74) *Attorney, Agent, or Firm* — Tucker Law, P.A.; Matthew Sean Tucker, Esq.

(57) ABSTRACT

A surgical pin compression wound dressing stabilizing system includes a compressive wound dressing module having a central orifice and radial slit, and a stabilizing device formed of a single piece of material having a longitudinal passageway and a vertical slit, the slits allowing insertion of the module and stabilizing device on a surgical pin at a wound site with the surgical pin dispose in the orifice and passageway. The stabilizing device has an upright post with the longitudinal passageway and a bottom base with a recessed central cavity open at a bottom that receives and mates with an upper portion of the module. The bottom base has a lower outer annular surface surrounding the central cavity for engaging a peripheral rib on the module to enable application of an equal distribution of a downward compressive pressure on the module.

20 Claims, 22 Drawing Sheets

Related U.S. Application Data which is a continuation-in-part of application No. 13/066,719, filed on Apr. 23, 2011, now Pat. No. 9,730,696.

(58) Field of Classification Search
CPC ...... A61B 2034/102; A61B 2090/3983; A61B 42/00; A61B 2017/00893; A61B 17/1746; A61B 2034/2051; A61B 2090/396666; A61B 2017/00889; A61B 17/154; A61B 90/39; A61B 17/07292; A61B 2017/07271; A61B 2017/3937; A61B 90/98; A61B 2017/00495; A61B 2017/00898; A61B 2017/07257; A61B 2017/1132; A61B 17/0643; A61B 17/1757; A61B 17/848; A61B 2017/00725; A61B 2034/256; A61B 2090/3614; A61B 2090/371; A61B 2090/3735; A61B 2090/397; A61B 34/25; A61B 17/0487; A61B 17/1714; A61B 2017/0462; A61B 34/30; A61B 5/4514; A61B 17/06; A61B 17/142; A61B 17/7225; A61B 18/1442; A61B 2017/00707; A61B 2034/252; A61B 2090/061; A61B 2090/309; A61B 2090/366; A61B 2090/3908; A61B 2090/3991; A61B 6/14; A61B 6/584; A61B 90/92; A61B 90/94; A61B 17/12099; A61B 17/1725; A61B 17/7098; A61B 17/7291; A61B 18/04; A61B 18/082; A61B 2017/00867; A61B 2017/0412; A61F 13/36; A61F 13/041; A61F 13/79009; A61F 15/00; A61F 15/006

See application file for complete search history.

(56) References Cited

U.S. PATENT DOCUMENTS

| | | | | |
|---|---|---|---|---|
| 4,943,293 | A * | 7/1990 | Lee, Jr. | A61B 17/60 128/888 |
| 5,050,661 | A * | 9/1991 | Sikkema | E06B 9/24 160/84.07 |
| 5,360,020 | A * | 11/1994 | Lee, Sr. | A61B 17/60 128/888 |
| 5,702,388 | A * | 12/1997 | Jackson | A61B 17/685 24/115 G |
| 5,833,666 | A * | 11/1998 | Davis | A61M 25/02 604/180 |
| 8,454,603 | B2 * | 6/2013 | Webb | A61B 17/864 606/304 |
| 9,050,136 | B2 * | 6/2015 | Webb | A61B 17/66 |
| 10,695,237 | B1 * | 6/2020 | Sanders, Jr. | A61F 13/00068 |
| 2005/0049596 | A1 * | 3/2005 | Stewart | A61B 17/685 606/302 |
| 2012/0271216 | A1 * | 10/2012 | Sanders, Jr. | A61B 17/08 602/60 |

* cited by examiner

SURGICAL PIN COMPRESSABLE WOUND DRESSING MODULE, DEVICE, AND SYSTEM

CROSS-REFERENCE TO RELATED APPLICATION

This U.S. non-provisional patent application is a continuation-in-part of, and claims priority and benefit to U.S. non-provisional patent application Ser. No. 13/066,719 filed by the same inventor on Apr. 23, 2011 and Ser. No. 15/646,930 filed by the same inventor on Jul. 11, 2017. The entire contents of U.S. patent application Ser. No. 13/066,719 and Ser. No. 15/646,930 are incorporated-by-reference herein in their entirety.

FIELD OF THE INVENTION

The present invention relates to the field of surgery where surgical pins (hereinafter used in a generic sense to mean pins or wires) are utilized and, more particularly, is concerned with a surgical pin compression wound dressing module, device and system.

BACKGROUND OF THE INVENTION

Surgical procedures are often performed to fixate fractured bones or to secure an anatomical stabilization device, such as a halo or external fixator. Surgical pin placement involves inserting a portion of the surgical pin through the patient's skin and into a bone while allowing a portion of the surgical pin to extend outward from the patient's skin. The exposed pin allows a fixation device to be attached. These surgical pins must remain in position for some period of time depending on their intended purpose.

Prior approaches, such as disclosed in U.S. Pat. Nos. 4,943,293, 5,360,020, 5,702,388 and 8,216,288, include the utilization of devices, such as collars, retainers or clips, to stabilize a wound dressing or sponge in place over a surgical pin site. These devices are deficient in three main areas.

A first main area of deficiency is the lack of symmetrical wound compression. Adequate wound compression is directly related to the precise geometric coupling between the wound dressing and wound dressing stabilization device being used. These prior art approaches lack an adequate wound dressing housing and therefore provide asymmetric wound compression. Such asymmetry could lead to unequal skin tension and possible skin breakdown and soft tissue necrosis.

A second main area of deficiency is the lack of a closed wound dressing environment. Without the provision of a closed wound dressing environment drainage from the surgical pin site will communicate with the patient's adjacent skin. This in turn can allow bacteria upon a patient's skin to track into the surgical pin site causing a subsequent infection.

A third main area of deficiency is the failure to provide sufficient stabilizing of the surgical pin. Poor stabilizing of the surgical pin is first due to the inability of the collars, retainers or clips to maintain adequate pressure on the patient's skin. Due to a lack of rigidity, and the inherent pliability of wound dressing materials, most of the downward pressure needed to stabilize the surgical pin is absorbed by the wound dressing or sponge. Also, the close proximity between the securing devices, e.g. the collars, retainers or clips, with the wound dressing material being used provides an inferior point of fixation.

Furthermore, specific problems following the application of surgical fixation pins occur in aftercare relating to pin site wound dressings. Ordinary wound dressings lack wound compression, leading to excessive bleeding and drainage around the pin sites. Also, continuity of drainage soaked wound dressings with the patient's adjacent skin permits bacterial proliferation. Such proliferation allows bacteria from the skin outside the surgical pin site to be channeled into the surgical pin site. These circumstances set the stage for wound infections. In addition, the common method for changing and maintaining wound dressings around surgical pin sites is ineffective and laborious to say the least. Attempting to wrap sterile dressings around surgical pin sites does not provide adequate wound coverage or compression. For medical staff it is also a time-consuming process resulting in decreased time to care for other patients. For the patient, lack of compliance because of the complexity of changing their surgical pin site dressings at home results in leaving drainage-soaked pin site dressings on for days. These combined circumstances predispose the patient to wound infections. Furthermore, the high volume of disposable medical wound dressings used, and increased medical waste from daily dressing changes, will increase health carecosts.

Accordingly, there remains a need in the art for an innovation that will overcome the deficiencies of past approaches and the problems that remain unsolved.

SUMMARY OF THE INVENTION

The present invention is directed to an innovation that overcomes the deficiencies of the past approaches and the problems that remain unsolved by providing a surgical pin compression wound dressing module, device and system. A surgical pin compression wound dressing stabilizing device and system symmetrically compress the compressive wound dressing module so as to precisely fit and stabilize it about the surgical pin at the wound site while also stabilizing the surgical pin at the wound site. Also, the stabilizing device and system establish a closed environment about the surgical pin at the wound site in which the compressed compressive wound dressing module is confined and any wound drainage from the wound site is isolated and drained away from the patient's adjacent skin through the device.

Accordingly, in one aspect of the present invention, a surgical pin compression wound dressing stabilizing device includes:
 an upstanding body having
  an upright post having an annular wall defining a longitudinal passageway through the upright post being open at opposite ends of the longitudinal passageway; and
  a bottom base rigidly connected to and extending outwardly from a lower portion of the upright post such that the upright post is centrally disposed relative to and extends upwardly above the bottom base, the bottom base defining a central cavity open at a bottom of the upstanding body that surrounds and communicates with the longitudinal passageway of the upright post and is recessed into the bottom base for mating with an upper portion of a compressive wound dressing module receivable into the central cavity;
 wherein the upright post and bottom base have a vertical slit separating the upstanding body into two halves to enable opening and closing and fitting of the upstanding body about a surgical pin projecting above a wound site with the surgical pin disposed through the longitudinal passageway and central cavity;

wherein, the bottom base also defines a lower outer annular surface surrounding the central cavity for engaging a peripheral rib on the compressive wound dressing module to enable application of an equal distribution of a downward compressive pressure by the bottom base of the upstanding body upon the compressive wound dressing module.

In another aspect of the present invention, the stabilizing device also includes:

a hinge attached at a peripheral location on the bottom base at an end of the vertical slit allowing the upstanding body to assume the opened and closed positions relative to the surgical pin; and a fastener in at least one of the two halves of the upstanding body for securing the upstanding body at a desired location along the surgical pin.

In another aspect of the present invention, the stabilizing device also includes:

a drainage port on the bottom base in communication with the central cavity of the bottom base to allow drainage from the wound site through the central cavity; and a cap for closing the drainage port adapted to be removed from and placed upon the drainage port.

In another aspect of the present invention, a surgical pin compression wound dressing module includes:

a main body composed of a compressive wound dressing, the main body having upper and lower surfaces spaced apart and extending generally parallel to one another and an outer circumferential surface extending between and merging with the upper and lower surfaces so as to form upper and lower corners of the main body, the main body also having a central orifice formed therethrough between and open at the upper and lower surfaces thereof; and a peripheral rib connected to, extending about and protruding radially outward from the outer circumferential surface of the main body, the peripheral rib being spaced from and located between the upper and lower corners of the main body and having top and bottom annular surfaces extending perpendicularly outward from the outer circumferential surface of the main body and terminating at an outer circumferential surface of the peripheral rib;

wherein the main body and peripheral rib have a radial slit therethrough from the outer circumferential surface of the peripheral rib to the central orifice of the main body to enable opening of the main body and peripheral rib and fitting of the module about a surgical pin projecting above a wound site with the surgical pin disposed through the central orifice of the main body.

In another aspect of the present invention, the main body of the module is composed of a compressive wound dressing made of a sponge material.

In another aspect of the present invention, the peripheral rib is composed of the same compressive wound dressing as the main body.

In another aspect of the present invention, a surgical pin compression wound dressing stabilizing system includes:

a surgical pin compression wound dressing module including a main body composed of a compressive wound dressing, the main body having upper and lower surfaces spaced apart and extending generally parallel to one another and an outer circumferential surface extending between and merging with the upper and lower surfaces so as to form upper and lower corners of the main body, the main body also having a central orifice formed therethrough between and open at the upper and lower surfaces thereof, and a peripheral rib connected to, extending about and protruding radially outward from the outer circumferential surface of the main body, the peripheral rib being spaced from and located between the upper and lower corners of the main body and having top and bottom annular surfaces extending perpendicularly outward from the outer circumferential surface of the main body and terminating at an outer circumferential surface of the peripheral rib, wherein the main body and peripheral rib have a radial slit therethrough from the outer circumferential surface of the peripheral rib to the central orifice of the main body to enable opening of the main body and peripheral rib and fitting the module about a surgical pin projecting above a wound site with the surgical pin disposed through the central orifice of the main body; and a surgical pin compression wound dressing stabilizing device including an upstanding body having an upright post having an annular wall defining a longitudinal passageway through the upright post being open at opposite ends of the longitudinal passageway, and a bottom base rigidly connected to and tapering outwardly and downwardly from a lower portion of the upright post such that the upright post is centrally disposed relative to and extends upwardly above the bottom base, the bottom base defining a central cavity open at a bottom of the upstanding body that surrounds and communicates with the longitudinal passageway of the upright post and is recessed into the bottom base for mating with an upper portion of the compressive wound dressing module above the top annular surface of the peripheral rim of the compressive wound dressing module, wherein the upright post and the bottom base have a vertical slit separating the upstanding body into two halves to enable opening and closing and fitting of the upstanding body about the surgical pin above the wound site with the surgical pin disposed through the longitudinal passageway and central cavity, wherein the bottom base also defines a lower outer annular surface surrounding the central cavity for engaging the peripheral rib on the compressive wound dressing module to enable application of an equal distribution of a downward compressive pressure by the upstanding body upon the compressive wound dressing module, a hinge attached at a peripheral location on the bottom base at an end of the vertical slit allowing the upstanding body to assume the opened and closed positions relative to the surgical pin, a fastener in at least one of the two halves of the upstanding body for securing the upstanding body at a desired location along the surgical pin, and a drainage port on the bottom base in communication with the central cavity of the bottom base to allow drainage from the wound site through the central cavity.

These and other aspects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, in which.

Like reference numbers refer to like parts throughout the several views of the drawings.

DETAILED DESCRIPTION OF EXEMPLARY IMPLEMENTATIONS

Figure 1:
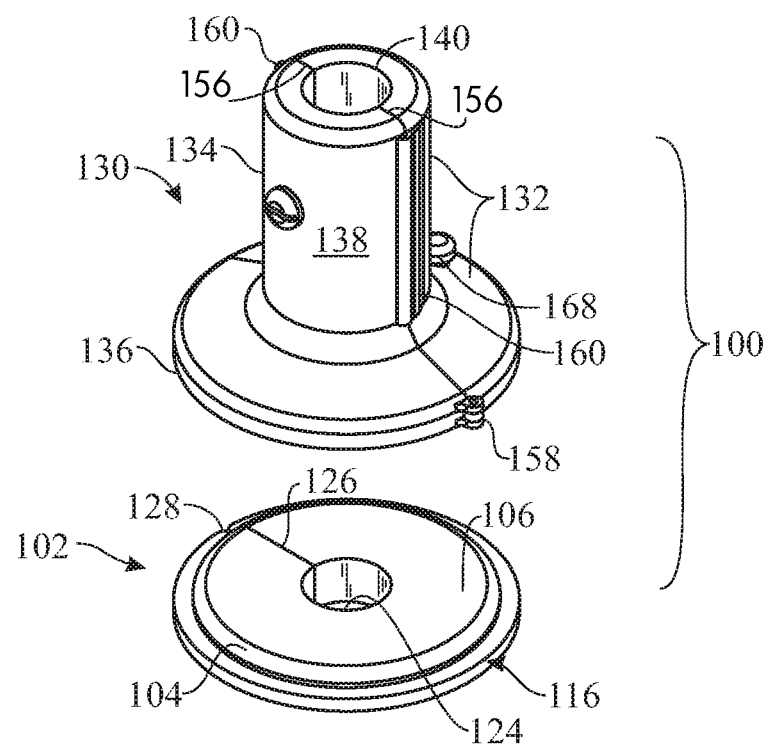
FIG. 1 presents an upper isometric view of an exemplary embodiment of a surgical pin compression wound dressing device and system in accordance with aspects of the present invention, wherein a surgical pin compression wound dressing module and the device of the system are shown in their respective closed states aligned with, but displaced from, one another.
Figure 2:
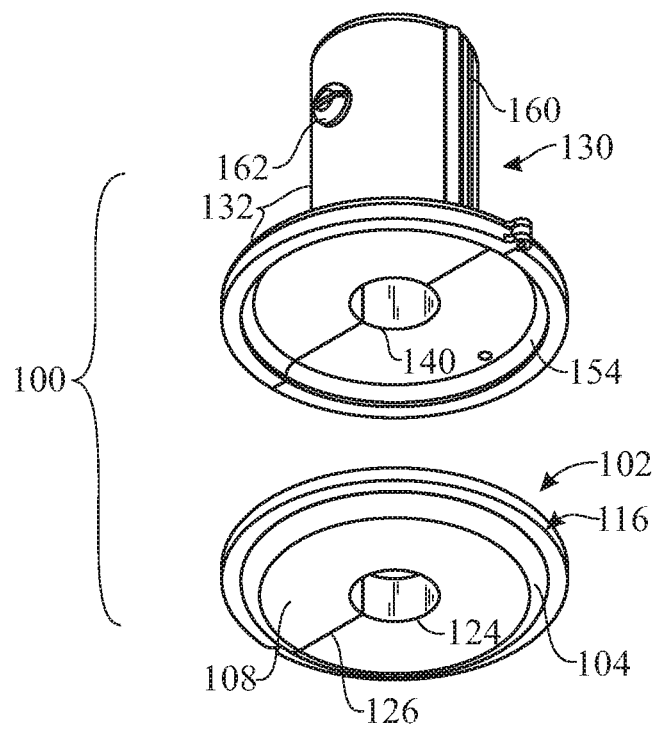
FIG. 2 presents a lower isometric view of the surgical pin compression wound dressing module and device of the system originally introduced in FIG. 1.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The present invention provides an effective, easy to use a surgical pin compression wound dressing module, device and system that will stabilize a surgical orthopedic pin utilized during medical procedures, while simultaneously providing the compressive wound dressing module symmetrically compressed by the surgical pin compression wound dressing device at the wound site where such surgical pin is introduced into the patient's skin. As the surgical pin at the entry site passes through the skin and into the bone, deeper soft tissues and the bone itself are prone to infection. Surgical pin movement within the pin entry site during patient movement is also a cause of tissue breakdown which can result in a higher incidence of infection. Thus, tissue breakdown and resultant wound damage become issues with regards to wound infections. The protective action of the surgical pin compression wound dressing module, device and system, described hereinafter with reference to the drawings, addresses these issues.

Referring to FIGS. 1-12, there is illustrated an exemplary embodiment of a surgical pin compression wound dressing system in accordance with aspects of the present invention. Basically, the surgical pin compression wound dressing system, generally designated as reference numeral 100, has two main components. The first of the two main components of the system 100 is a surgical pin compression wound dressing module 102. As seen in FIGS. 1-5, the wound dressing module 102 has a main body 104 composed of a compressive wound dressing, preferably in the form of a conventional sponge material having a predetermined configuration and size customized in accordance with the requirements of the patient's wound site 200 and the particular surgical pin 202 at the wound site. The main body 104 of the module 102 has upper and lower surfaces 106, 108, spaced apart and extending generally parallel to one another, and an outer circumferential surface 110 extending between and merging with the upper and lower surfaces so as to form upper and lower annular rounded corners 112, 114 of the main body.

Preferably, the wound dressing module 102 has a peripheral rib 116 integrally connected to and extending about the outer circumferential surface 110 of the main body 104. The peripheral rib 116 is spaced from and located between the rounded upper and lower corners 112, 114 of the main body 104. The peripheral rib 116 has an annular configuration that protrudes from the outer peripheral surface 110 of the main body 104, and has top and bottom annular surfaces 118, 120 extending perpendicularly outward from the outer peripheral surface 110 of the main body 104, terminating at an outer circumferential surface 122 of the peripheral rib. The peripheral rib 116 may be composed of the same compressive wound dressing sponge material and may have the same predetermined configuration as the main body 104.

Further, the wound dressing module 102 may have a central orifice 124 extending through main body 104 between, and open at, the upper and lower surfaces 106, 108 thereof. The cross-sectional configuration of the central orifice 124 may be the same as that of the particular surgical pin 202 at the wound site 200, such as cylindrical or other suitable geometric shape. The main body 104 and peripheral rib 116 of the module 102 have a radial slit 126 formed through and extending from an outer V-shaped entrance 128, provided in the outer circumferential surface 122 of the peripheral rib 116, to the central orifice 124 of the main body 104. The radial slit 126 in the module 102 enables opening of the main body 104 and peripheral rib 116 of the module sufficiently to allow fitting of the module about the surgical pin 202 projecting above the wound site 200 with the surgical pin disposed through the central orifice 124 of the main body. In an alternate implementation, lower surface 108 of wound dressing module main body 102 could incorporate a concave surface in lieu of the planar lower surface 108 shown in the accompanying figures. Furthermore, it will be apparent to those skilled in the art that rounded corners 112 and 114 could be provided squared off, beveled or incorporating any other surface geometry consistent with the operation of the invention.

The second of the two main components of the system 100 is a surgical pin compression wound dressing stabilizing device 130. As seen in FIGS. 6-8, 10 and 11, the stabilizing device 130 is configured to surround and allow adjustment along the surgical pin 202 in order to select a stationary position thereon at which to attach the stabilizing device to the surgical pin so as to thereby maintain or stabilize the surgical pin in an upright stationary orientation and concurrently compress and confine the wound dressing module 102 in a closed environment. The stabilizing device 130 includes an upstanding body 132 having an upright post 134 and a bottom base 136 being rigidly connected to one another such that the upright post is centrally disposed relative to and extends upwardly above the bottom base.

Figure 3:
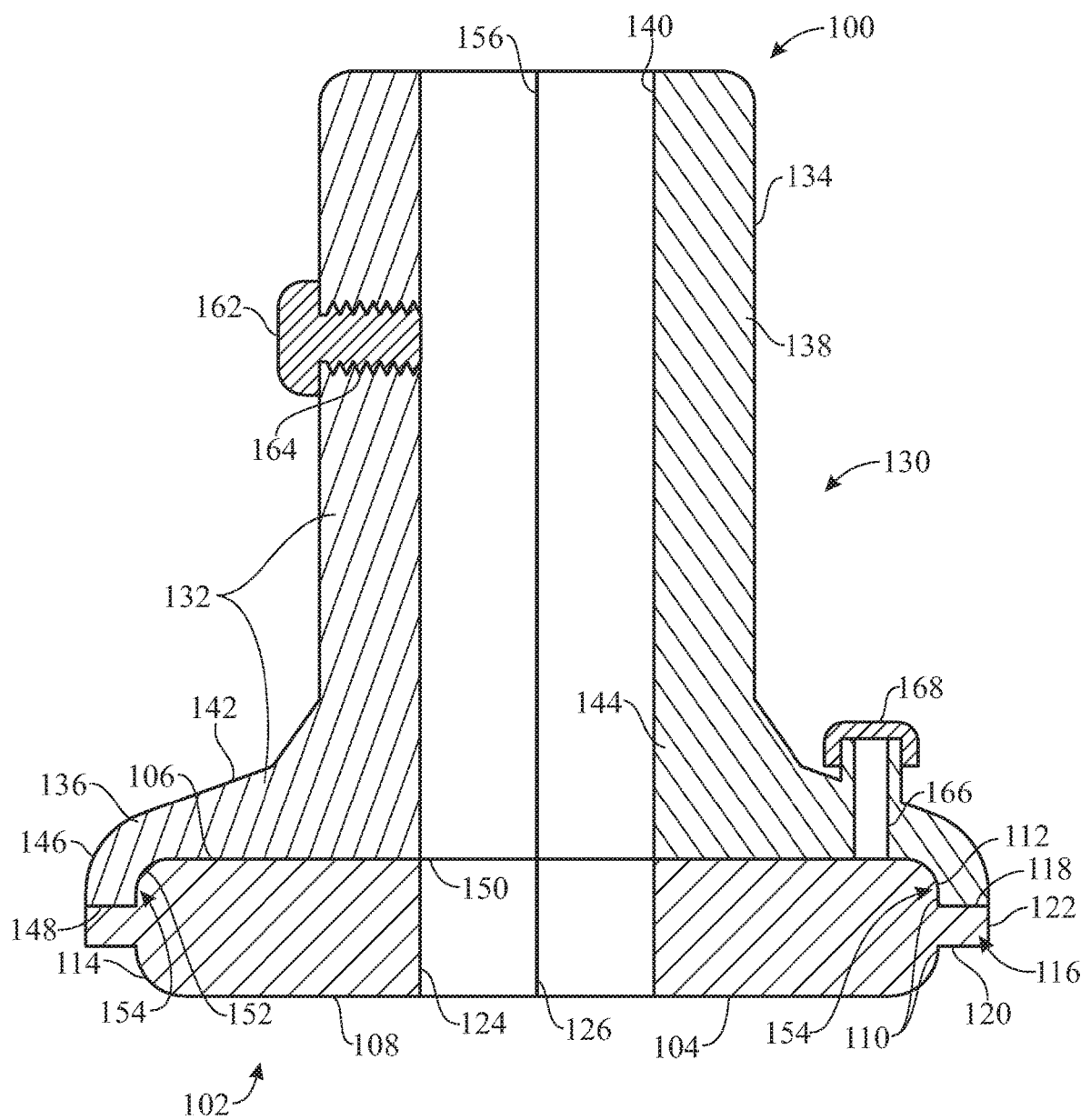
FIG. 3 presents a longitudinal sectional view of the surgical pin compression wound dressing module and device of the system originally introduced in FIG. 1 but when in their respective closed states with one another.
Figure 10:
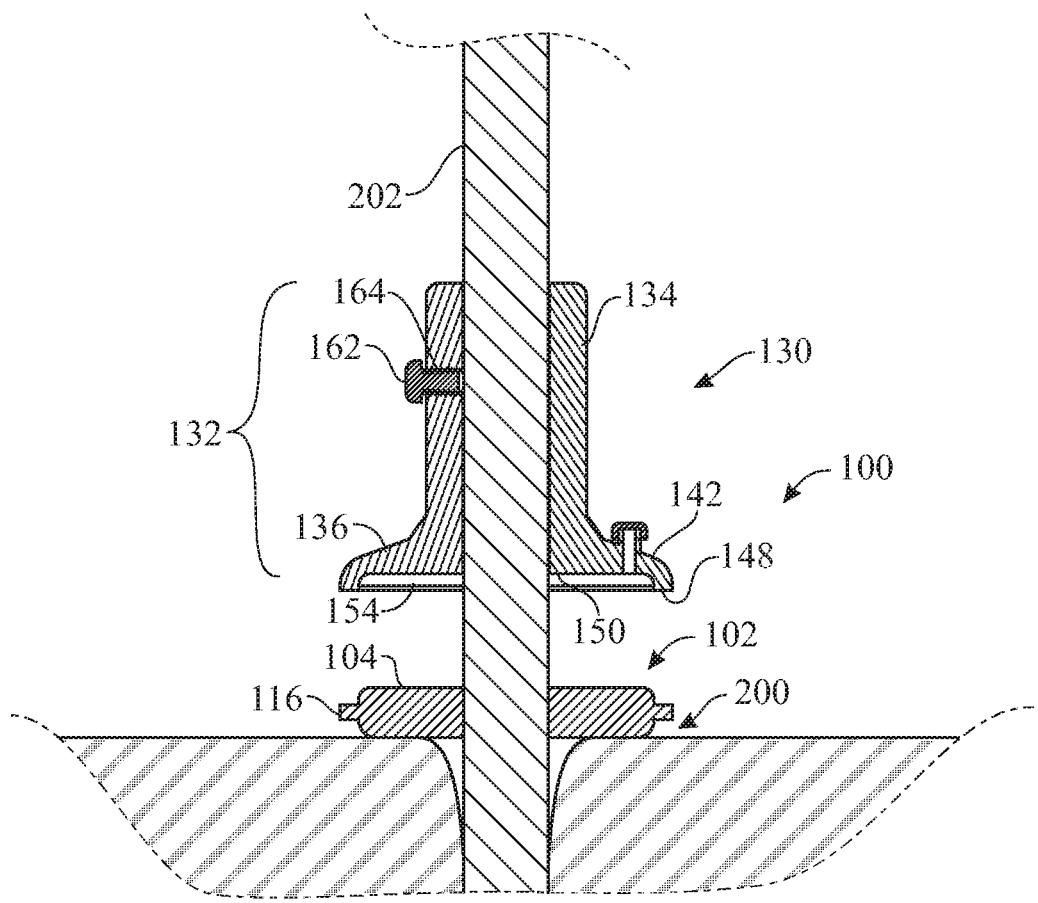
FIG. 10 presents a longitudinal sectional view of the surgical pin compression wound dressing module and device of the system, illustrating the device displaced above the wound dressing module.
Figure 11:
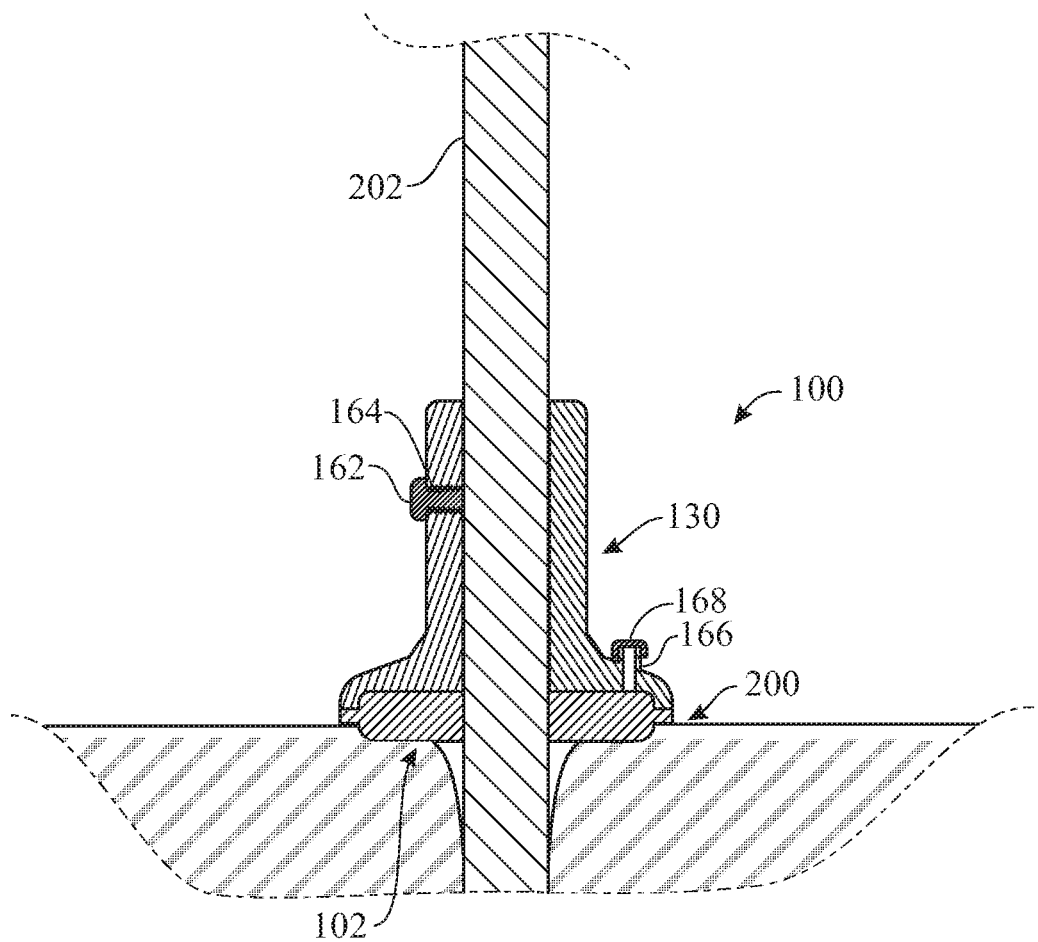
FIG. 11 presents another longitudinal sectional view of the surgical pin compression wound dressing module and device of the system, illustrating the device compressing the compressive wound dressing module partially into the flesh of a patient about the surgical pin.

More particularly, as seen in FIGS. 3, 10 and 11, the upright post 134 of the upstanding body 132 has an annular wall 138 defining a longitudinal passageway 140 through the upstanding body that has a cross-sectional size generally the same as the cross-sectional size of the central orifice 124 through the main body 104 of the wound dressing module 102 such that both will slidably fit about the surgical pin 202. The bottom base 136 of the upstanding body 132 has an upper surface 142 that tapers outwardly and downwardly from a lower end portion 144 of the upright post 134 of the upstanding body, terminating in a rounded peripheral portion 146 on the bottom base. The bottom base 136 of the upstanding body 132 also has a lower outer annular surface 148 that aligns with the top annular surface 118 of the peripheral rib 116 on the wound dressing module 102.

The bottom base 136 of the upstanding body 132 further has a lower inner annular surface 150 and a lower intermediate annular surface 152 extending between and interconnecting the lower outer and inner annular surfaces 148, 150. The lower inner annular surface 150 is recessed into the bottom base 136 relative to its lower outer annular surface 148. The lower intermediate annular surface 152 of the bottom base 136 is arcuate in configuration. The lower inner and intermediate annular surfaces 150, 152 of the bottom base 136 together define a central cavity 154 that is open downwardly from the bottom base 136 and recessed into the bottom base. The central cavity 154 surrounds and communicates with the longitudinal passageway 140 through the upright post 134 of the upstanding body 132. As seen in FIGS. 3, 10 and 11, the lower outer, lower inner and lower intermediate annular surfaces 148, 150, 152 of the bottom base 136 align and are mateable with the upper side of the compressive wound dressing module 102, namely the top annular surface 118 of the peripheral rib 116 of the module, the upper surface 106 of the main body 104 of the module and the upper rounded edge 112 of the main body of the module.

Figure 6:
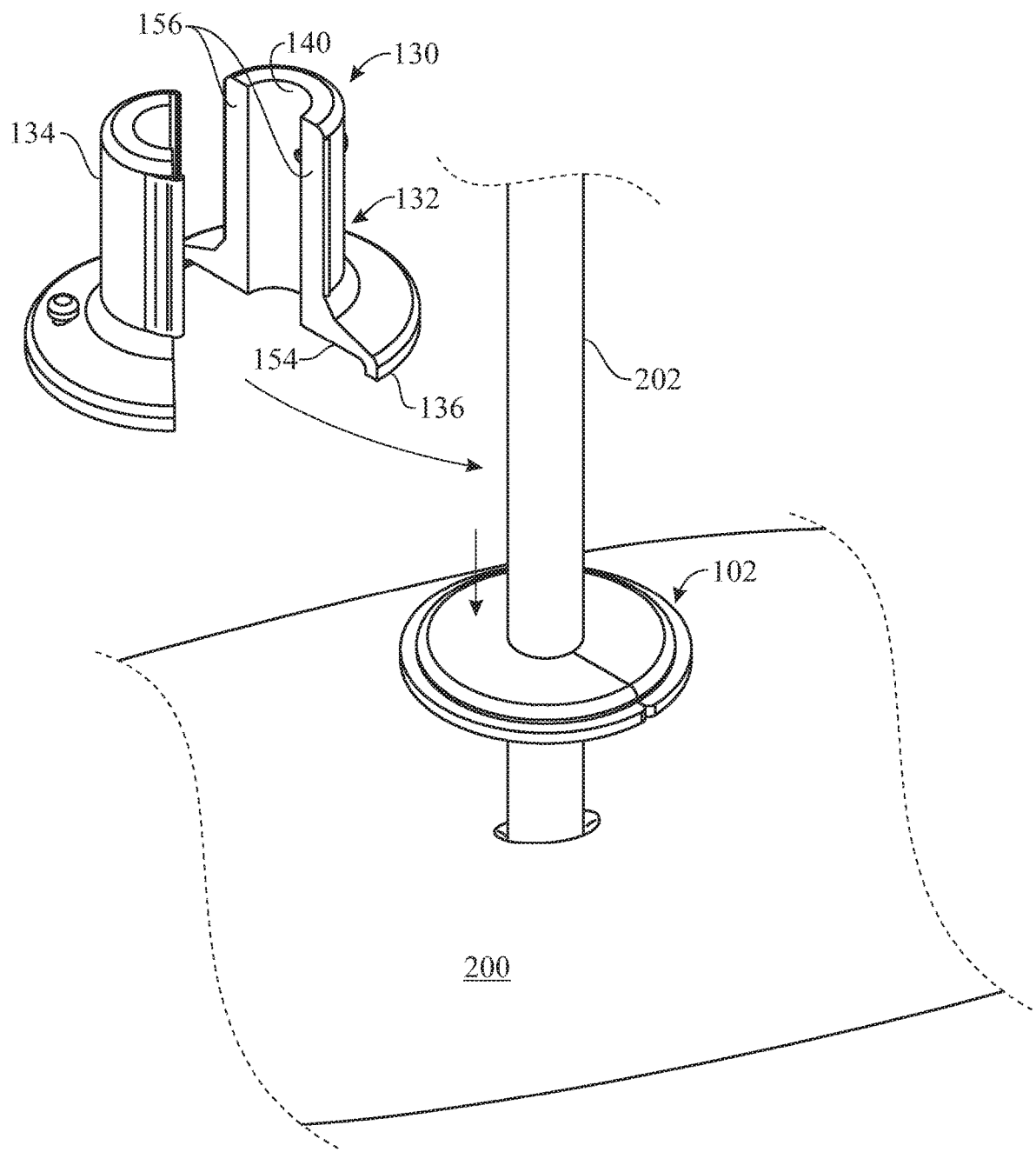
Figure 7:
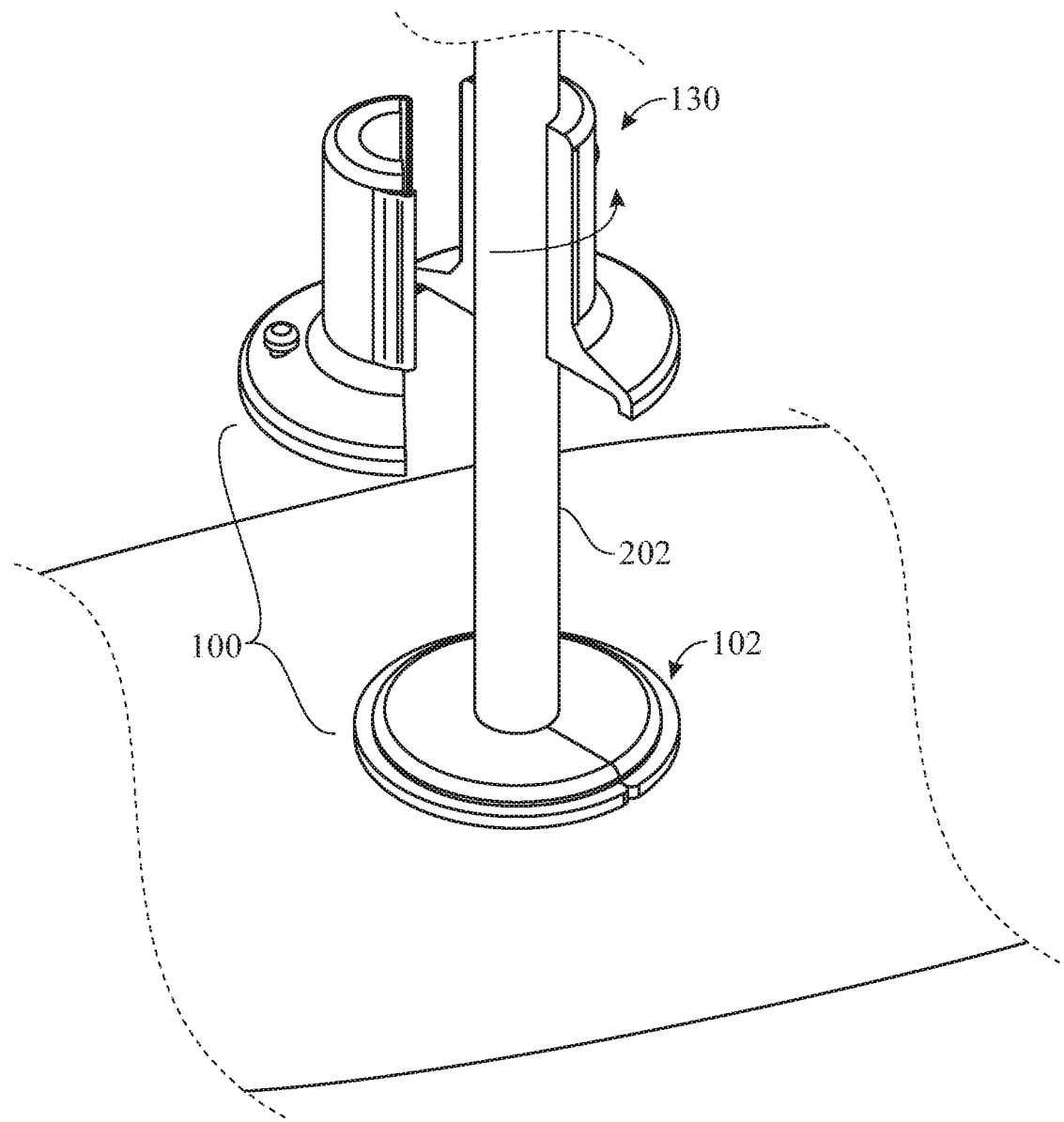
Figure 8:
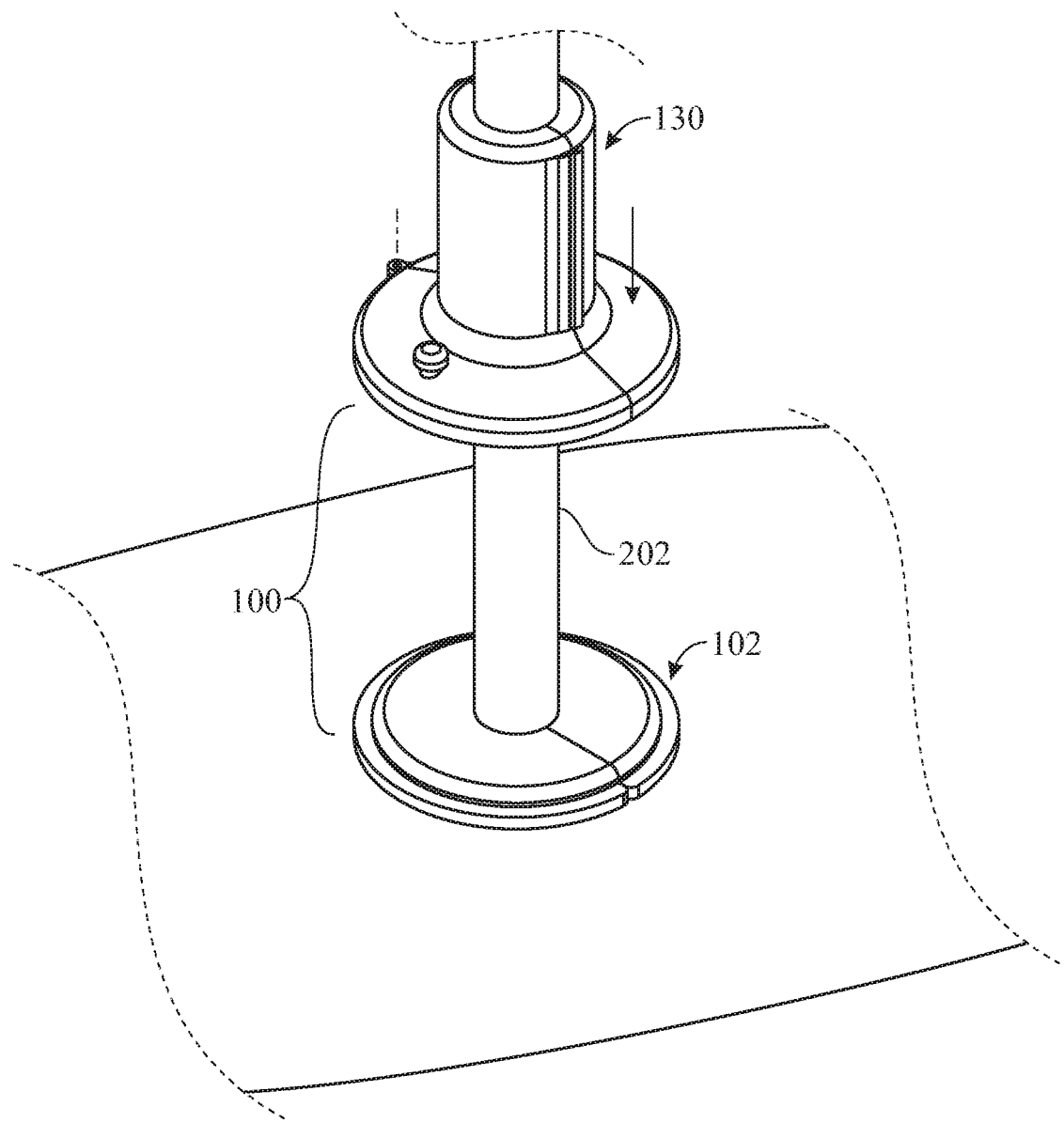
Figure 9:
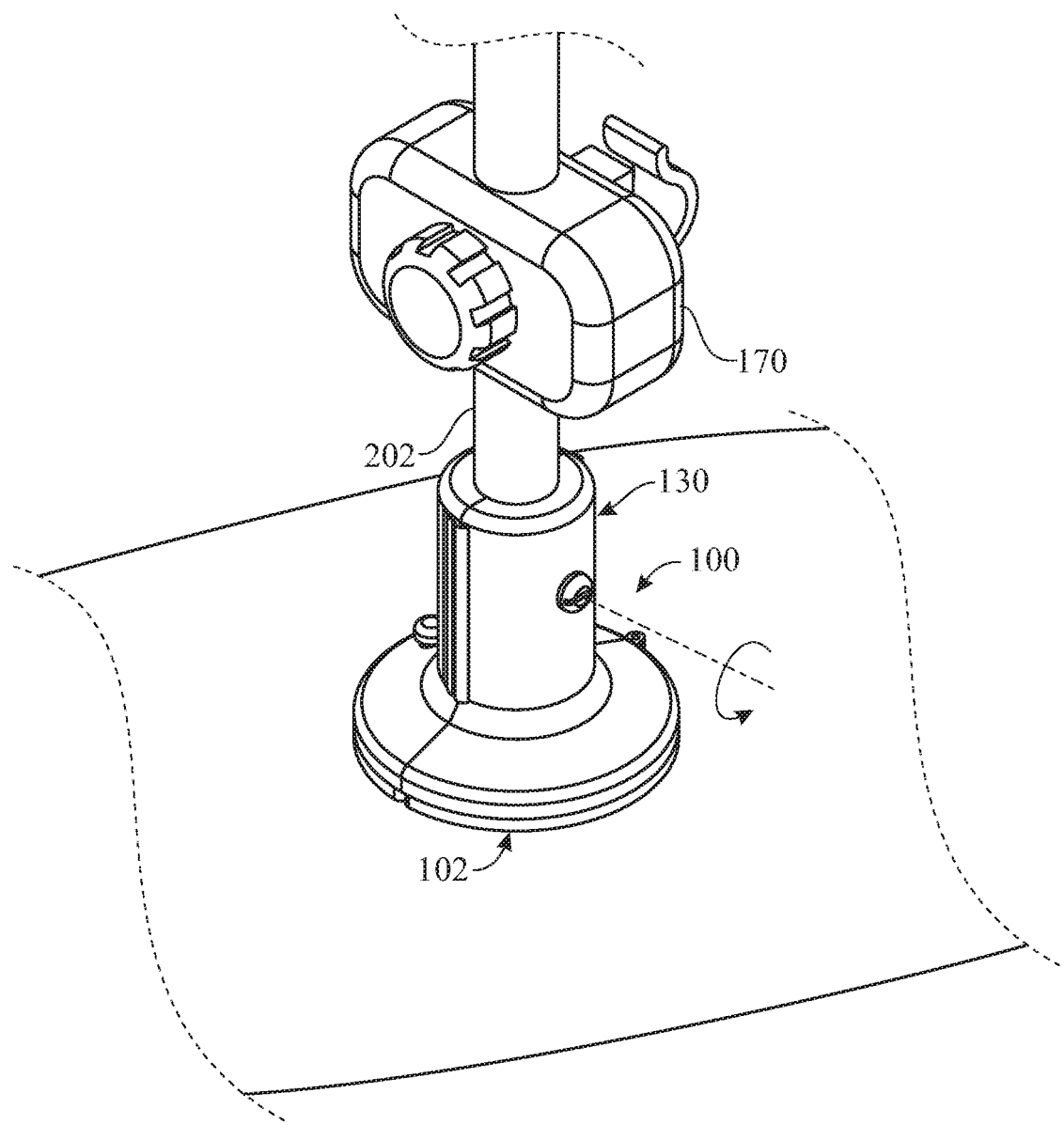

The upright post 134 and bottom base 136 of the upstanding body 132 of the stabilizing device 130 have a vertical slit 156, which separates the upstanding body into two halves pivotally connected together by a hinge 158 attached at a peripheral location on the bottom base 136 at one end of the vertical slit 156. The hinge 158 allows the upstanding body 132 of the stabilizing device 130 to assume opened and closed positions relative to the surgical pin 202, as seen in FIGS. 6-8. The vertical slit 156 of the stabilizing device 130 also is alignable with the radial slit 126 of the compressible wound dressing module 102. As shown in FIGS. 6 and 7, the vertical slit 156 enables opening and closing and fitting of the upstanding body 132 through the vertical slit and about the surgical pin 202 above the wound site 200 with the surgical pin disposed through the longitudinal passageway and central cavity.

Figure 12:
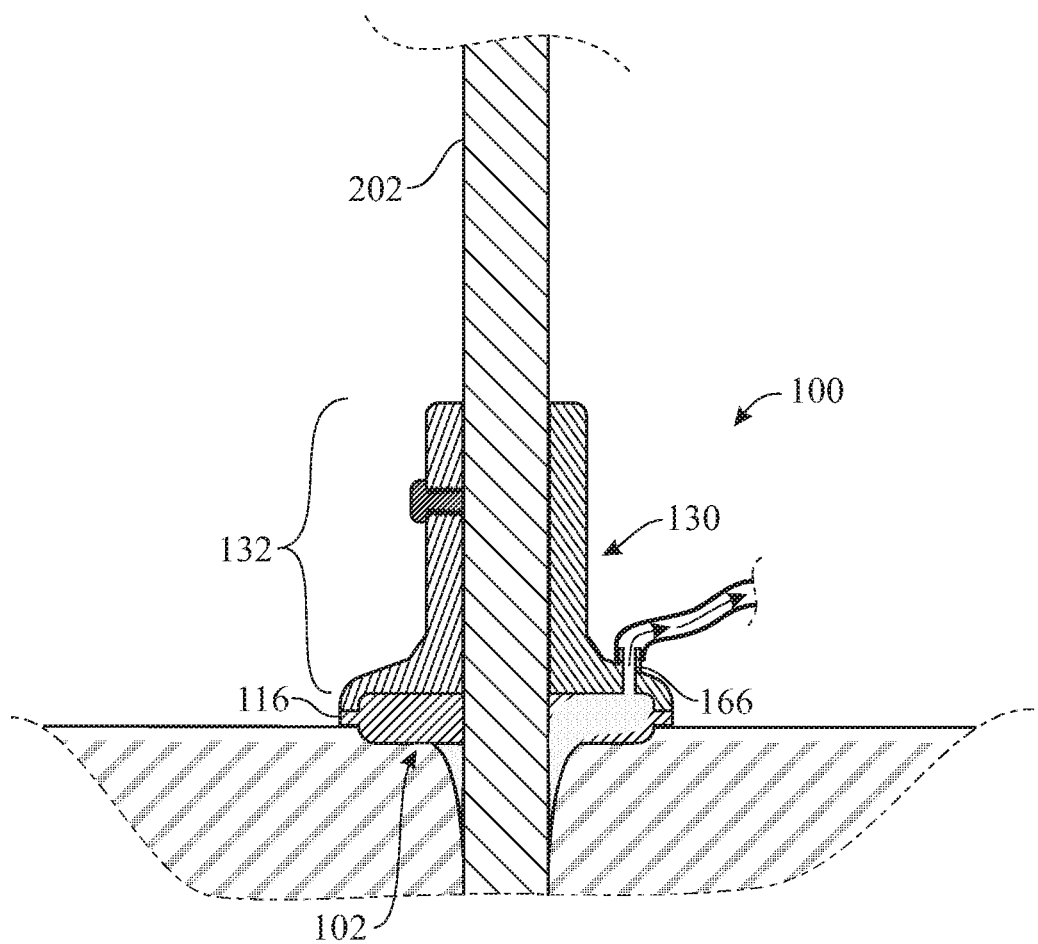
FIG. 12 presents still another longitudinal sectional view of the surgical pin compression wound dressing module and device of the system, illustrating evacuating drainage from the wound site through the device of the system.

The upright post 134 of the upstanding body 132 of the stabilizing device 130 has closure snaps or clasps 160 (see FIGS. 1-2) thereon at the opposite ends of the vertical slit 156 for releasing or securing the two halves of the upstanding body from or to one another. These clasps 160 are designed to allow a user to open and close the stabilizing device 130 with one hand. As best seen in FIGS. 10 and 11, one of the upright post halves has a fastener such as a set screw 162 configured for threading engagement within a threaded bore 164 extending completely through the respective half of the upright post 134 to enable contact with the surgical pin 202 so as to secure the stabilizing device 130 at a desired location/position therealong, which may apply compression to the wound dressing module 102, as seen in FIGS. 11 and 12. Due the annular configuration of its upstanding body 132, the stabilizing device 130 is able to apply an equal distribution of force upon the compressible wound dressing module 102 when a downward pressure is imposed on the stabilizing device.

As seen in FIGS. 10-12, the bottom base 136 of the stabilizing device 130 has a drainage port 166 defined therein extending from the upper surface 142 to the lower inner annular surface 150 of the bottom base so as to provide communication from the compressive wound dressing module 102 in the central cavity 154 of the bottom base to the exterior of the stabilizing device 130 to thereby allow drainage from the central cavity 154. A cap 168 is provided for covering the drainage port 166 at the exterior portion thereof when not in use. The drainage port 166 may be a small diameter channel sized, shaped and otherwise configured for having a length of drainage tubing selectively attached thereto, such that the drainage tubing provides a communication pathway through bottom base 136 of upstanding body 132.

Functionally, the stabilizing device 130 isolates the surgical pin 202 and the surgical wound site 200 from potential contaminants originating from outside the wound site while also decreasing the amount of wound drainage. Furthermore, the stabilizing device 130 allows for a precise geometrical coupling with the compressible wound dressing module 102. As can be understood from the illustration of FIGS. 3, 11, and 12, typically the depth of the central cavity 154 of the bottom base 136 of the stabilizing device 130 is approximately ½ the width of the wound dressing module 102. This quality gives the stabilizing device 130 the potential to provide the desired compression of the wound dressing module 102.

The stabilizing device 130 may be made from a plastic material, preferably clear and capable of providing the device with rigid, non-pliable, structural characteristics. It would be advantageous to utilize a plastic material capable of withstanding conventional operating room sterilization techniques. Any conventional plastic molding process may be utilized to manufacture the stabilizing device 130.

Figure 13:
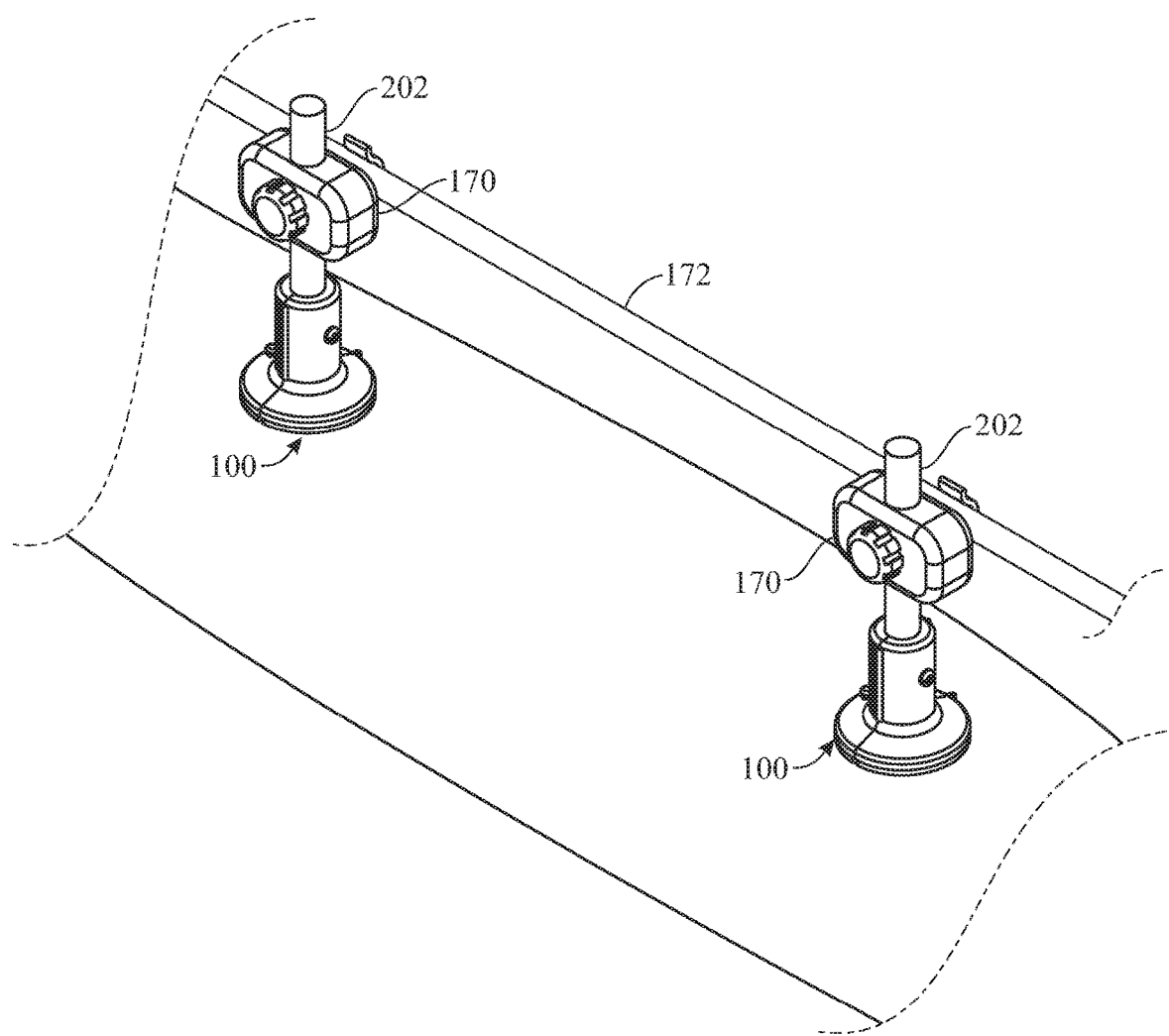

The above-described features of the stabilizing device 130 of the present invention embody the potential for numerous modifications or versions of the aforementioned description. All of the features are non-removable from the stabilizing device 130 with the exception of the cap 168 for the wound drainage port 166. However, by interchanging the position of the various features in relationship to the geometric configuration of the stabilizing device 130, the device would still operate the same. For example, by placing the hinge 156 on the opposite side of the bottom base 136 in comparison with the original location would not change the overall functional capabilities of the stabilizing device 130. Different versions of the system 100 would entertain the possibility of the wound dressing module 102 utilizing different types of wound dressing materials. The adaptability of the stabilizing device 130 would be directly related to the geometric shape, depth and diameter of the wound dressing module 102. For example, as alternatives to the circular shape, a wound dressing module 102 having a hexagonal shape may be employed for one type of wound dressing material and a square wound dressing module would be made to closely contour another type of wound dressing material. These versions having different geometric attributes that would coincide with the wound dressing material being used. Other modifications may be made in accordance with the working distance of two or more stabilizing devices 130 used simultaneously, as shown in FIG. 13, where surgical pins 202 may be interconnected by using clamps 170 and an elongated bar 172. The working distance of the device, or the distance at which two devices can be placed side by side, such as shown in FIG. 13, without interfering with one another, is directly related to the proximity of two adjacent surgical pins.

Figure 4:
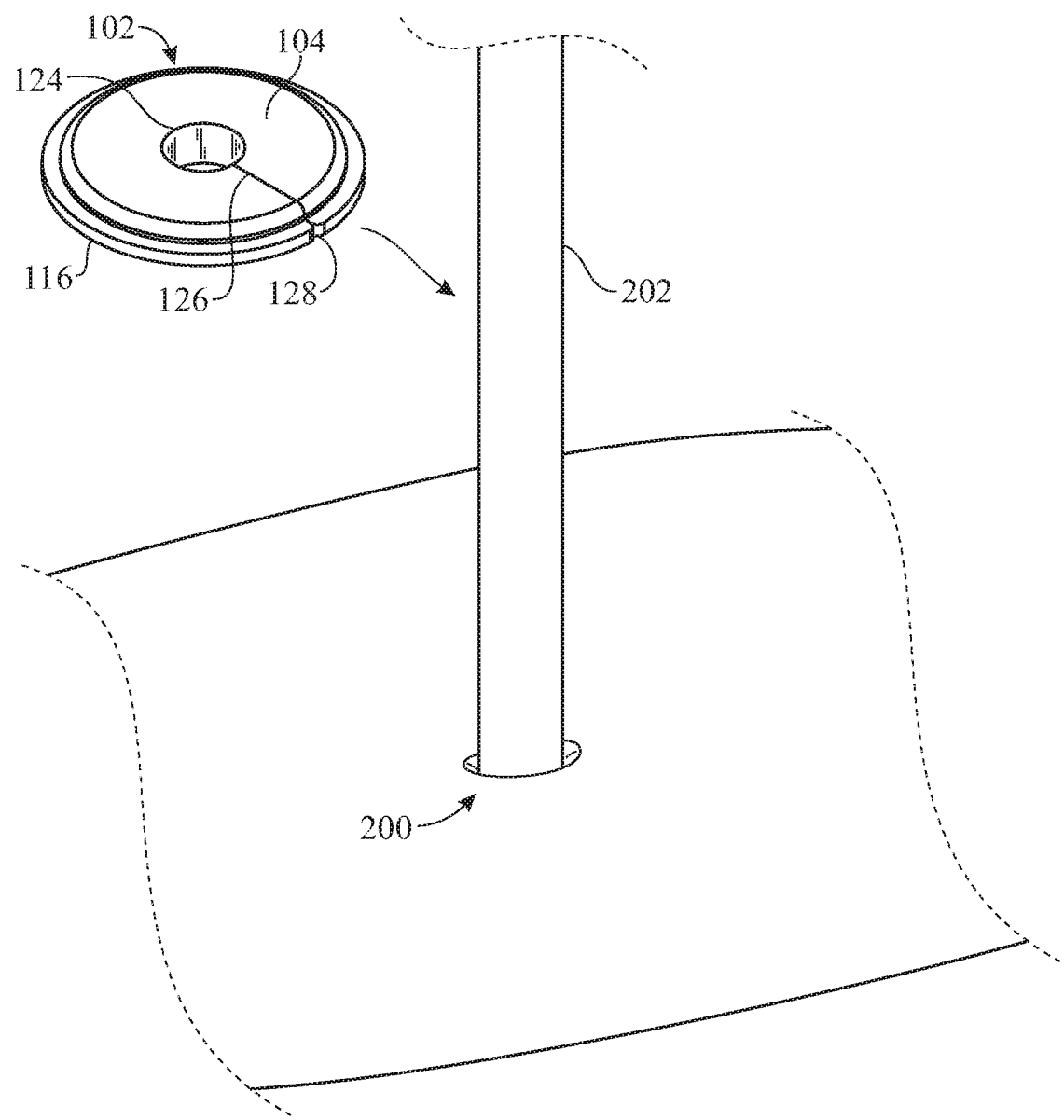
FIGS. 4-9 and 13 present upper isometric views of the surgical pin compression wound dressing module and device of the system at a succession of stages in stabilizing the wound dressing module and the surgical pin in accordance with aspects of the present invention.
Figure 5:
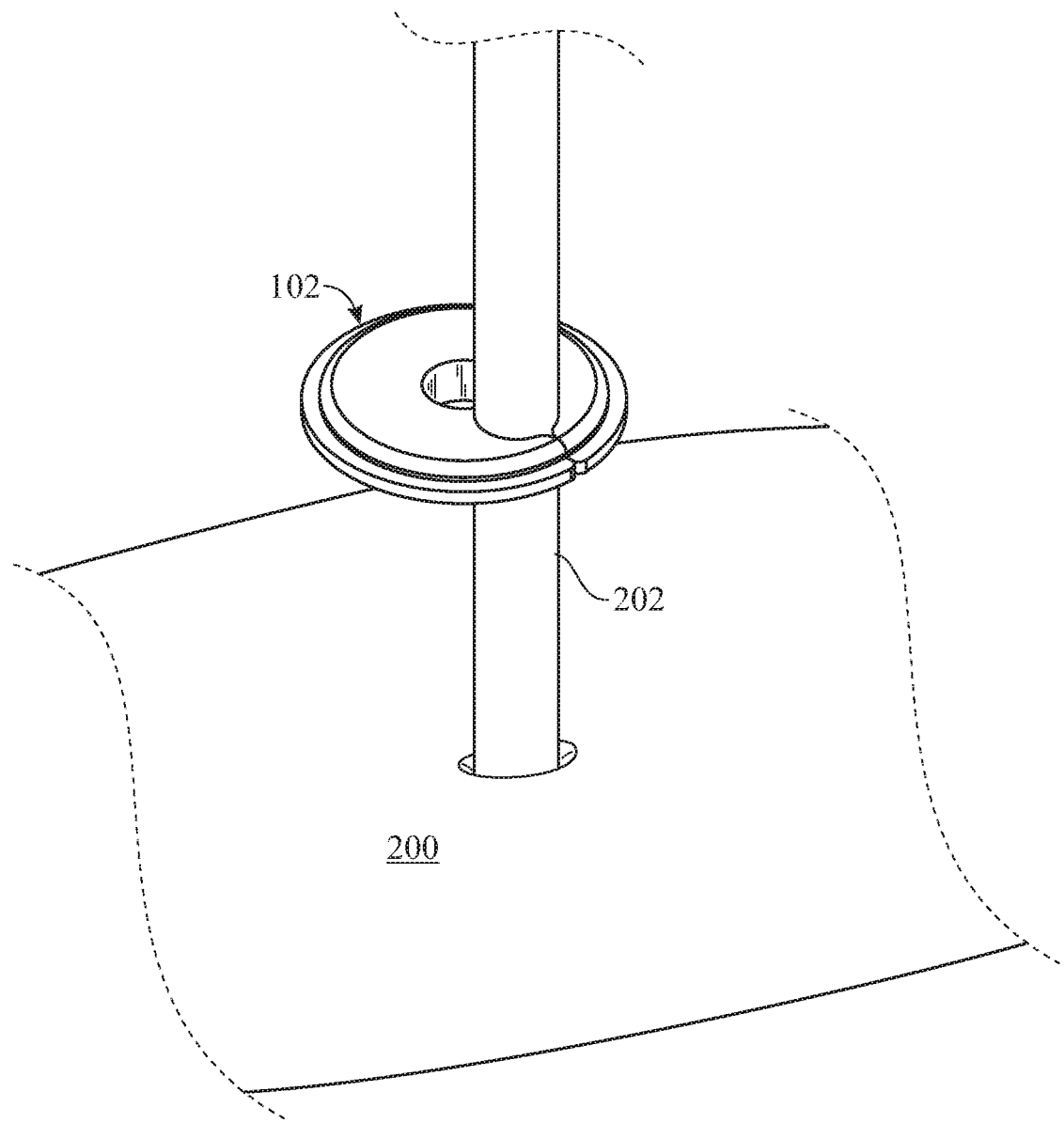

Referring now particularly to FIGS. 4-13, there is illustrated an exemplary implementation of a succession of stages of the system 100 for stabilizing the wound dressing module 102 and the surgical pin 202. Initially, a wound dressing module 102 of a predetermined size and geometry is inserted by a user about the surgical wire 202 at a location above the patient's skin at the wound site 200, as seen in FIGS. 4-6. Then, the wound dressing stabilizing device 130 is opened by the user, slipped about the surgical pin 202 and then closed, as best shown in FIGS. 6-8. Subsequently, the user can apply a downward force to the stabilizing device 130 in a direction toward the wound site 200, thereby engaging the lower outer annular surface 148 of the bottom base 136 of the stabilizing device 130 with the top annular surface 118 of the peripheral rib 116 of the wound dressing module 102. Preferably, this is accomplished in such a manner that the upper portion of the wound dressing module 102 is snugly received within central cavity 154 of the bottom base. Downward compression of the module 102 brings the bottom annular surface 120 of the peripheral rib 116 into contact with the patient's skin at the wound site 200, with the bottom portion of the main body 104 of the module 102 pressing against the flesh of the patient surrounding the wound site. The peripheral rib 116 acts as a buffer between the patient's skin and the stabilizing device 130. The amount of applied downward pressure will directly determine the corresponding degree of wound compression exerted upon the wound site of the patient. Finally, when a desired degree of wound compression is achieved, the user can simply adjust the set screw 162 to selectively secure the stabilizing device 130 against the surgical pin 202. Wound dressing module changes are easily performed by the health care provider or the patient by repeating the process mentioned above.

The surgical pin compressive wound dressing stabilizing device 130 is a biomedical mechanical device that allows for a compressive wound dressing to be applied and stabilized to the surgical pin sites of medical devices such as, for example, halos, external traction pins and other such devices that utilize surgical wires or pins. This medical device may be provided in any of a myriad of shapes, sized and configurations, without departing from the scope of the invention. However, the wound dressing module 102 is preferably provided having a geometry and size conforming to the central cavity 154 in the underside of the bottom base 136. Accordingly, the wound dressing modules 102 are preferably manufactured to custom fit corresponding pre-manufactured wound dressings. The closed environment provided by the wound dressing stabilizing device prevents wound drainage and helps prevent against bacterial contamination. Together the above-described two main components of the system 100 provide a means for applying wound compression to the wound site 200 of a surgical pin 202 while also stabilizing the surgical pin. Structurally, the rigid nature of the stabilizing device, as well as its precise fit as it couples with a specific wound dressing module, allows for symmetrical wound compression.

By providing a closed environment for the wound dressing material, the stabilizing device 130 acts to isolate the wound dressing module and its corresponding wound drainage from the patient's adjacent skin. Furthermore, the system 100 allows for surgical pin stability and also variability with regards to the amount of wound compression desired.

The easy use and effectiveness of the stabilization system 100 enable medical staff to become more efficient and waste less time with laborious ineffective tasks such as time-consuming wound dressing changes. Consequently, more time could be used for other patients resulting in an increase in the quality of patient care. For patients wound dressing changes at home after discharge from hospitals with surgical pins in place would be quite easily managed. The easy handling and manipulating of the stabilization system 100 allow all patients, even those lacking formal experience with post-surgical wound care methods, to properly care for their surgical wound sites. The decrease in both wound care supplies needed and medical waste generated, from the large quantity of discarded wound dressing bandages utilized, will ultimately cut health care costs.

The above-described embodiments are merely examples of implementations set forth for a clear understanding of the principles of the invention. Many variations, combinations, modifications or equivalents may be substituted for elements thereof without departing from the scope of the invention. Therefore, it is intended that the invention not be limited to the particular embodiments disclosed as the best mode contemplated for carrying out this invention, but that the invention will include all the embodiments falling within the scope of the appended claims.

By way of example, as will be apparent to those skilled in the art, the scope of the present invention is intended to include alternate implementations of the system incorporating multiple passageways through the wound dressing pin stabilization device 130 and the corresponding wound dressing module 102, where two or more adjacent pins are too closely located to one another to enable a multiple adjacent devices 100 to be utilized. That is, the system 100 can be produced in a modified version of the device for concurrently stabilizing more than one pin (e.g. where at least two adjacent pins sites are too close together to fit two of the wound dressing modules) in order to obtain desirable results without departing from the intended scope of the invention.

Figure 14:
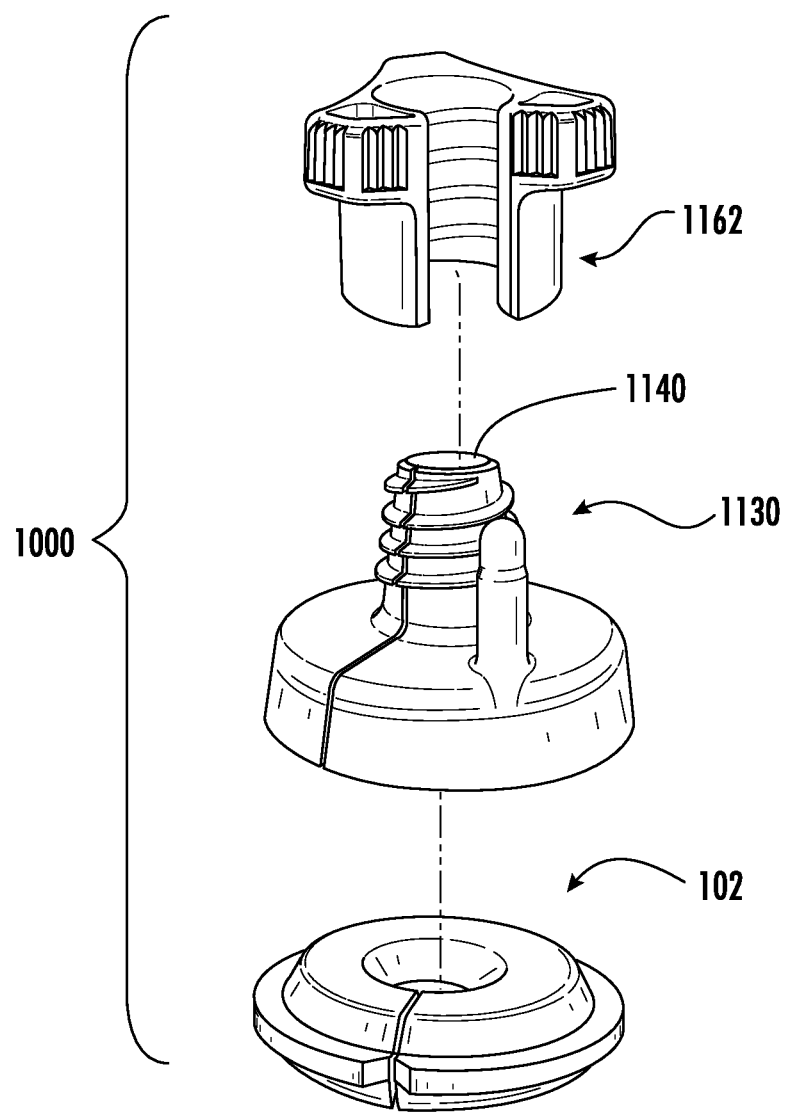
FIG. 14 presents an upper isometric view of an alternative exemplary embodiment of a surgical pin compression wound dressing device and system in accordance with aspects of the present invention, wherein a surgical pin compression wound dressing module and the stabilizing device and the securing screw of the system are shown in their respective states aligned with, but displaced from, one another.

Referring to FIG. 14, there is illustrated an alternative exemplary embodiment of a surgical pin compression wound dressing system in accordance with aspects of the present invention. Basically, the surgical pin compression wound dressing system, generally designated as reference numeral 1000, has three main components. The first of the three main components of the system 1000 is the surgical pin compression wound dressing module 102, as described above. Alternatively, the system may implement or use the angled wound dressing module 2102 (FIG. 22) as an alternative to the wound dressing module 102.

Figure 15:
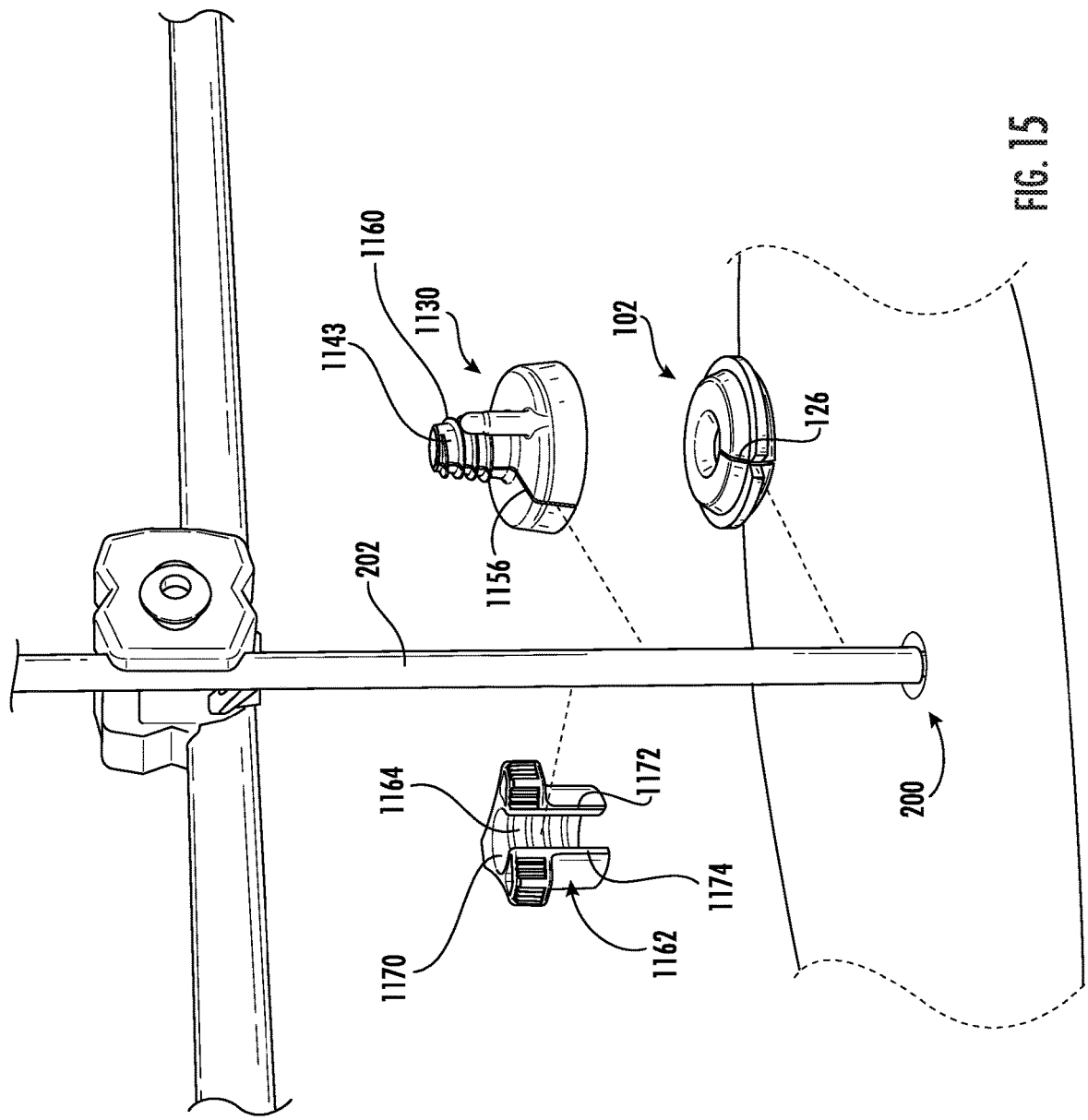
FIG. 15 presents an upper isometric view of the surgical pin compression wound dressing module and stabilizing device of the system at a succession of stages in stabilizing the wound dressing module and the surgical pin in accordance with aspects of the present embodiment of FIG. 14.
Figure 17:
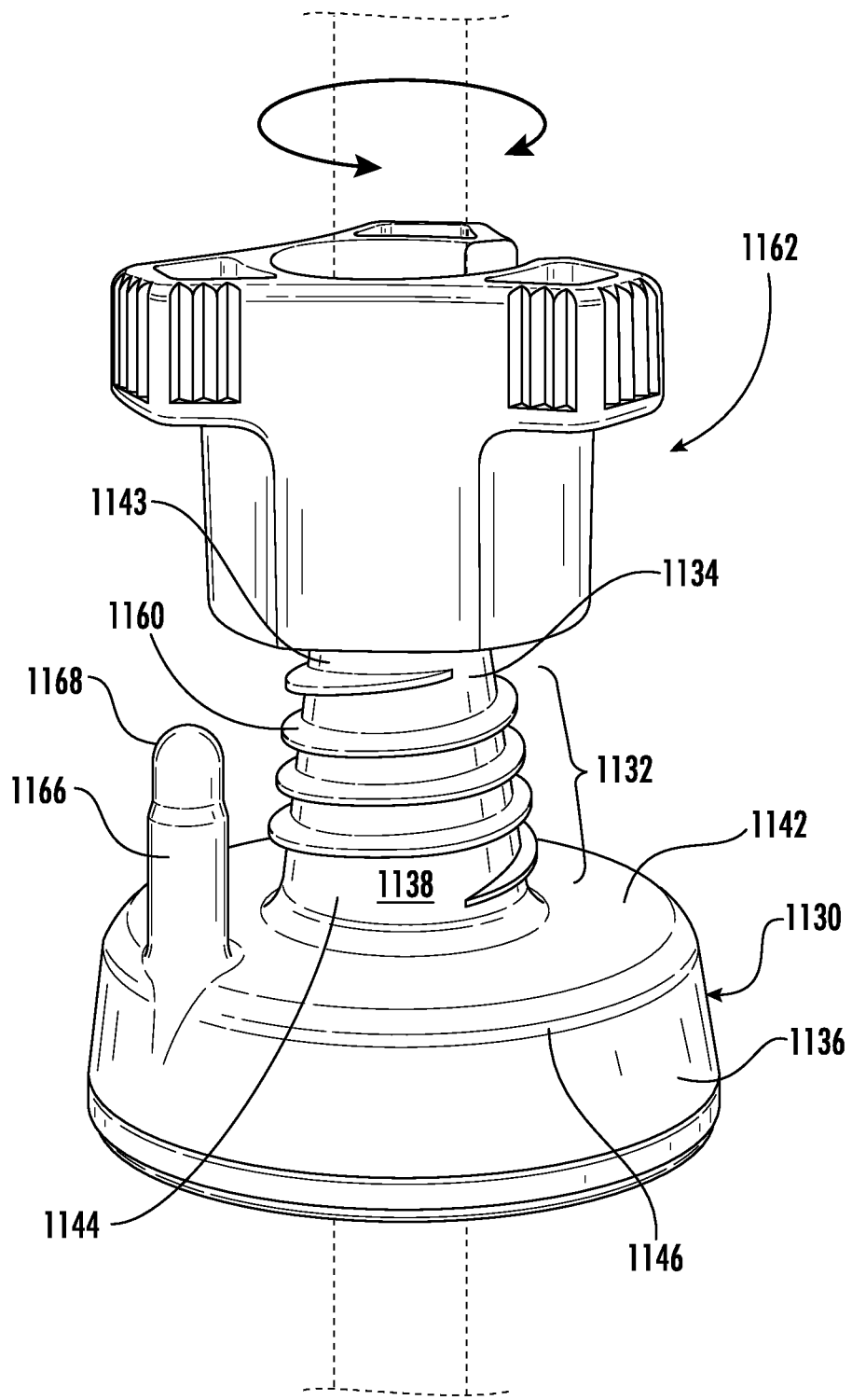
FIG. 17 presents an upper isometric view of the surgical pin compression wound dressing module and device of the system in accordance with one aspect of the present embodiment of FIG. 14.
Figure 18:
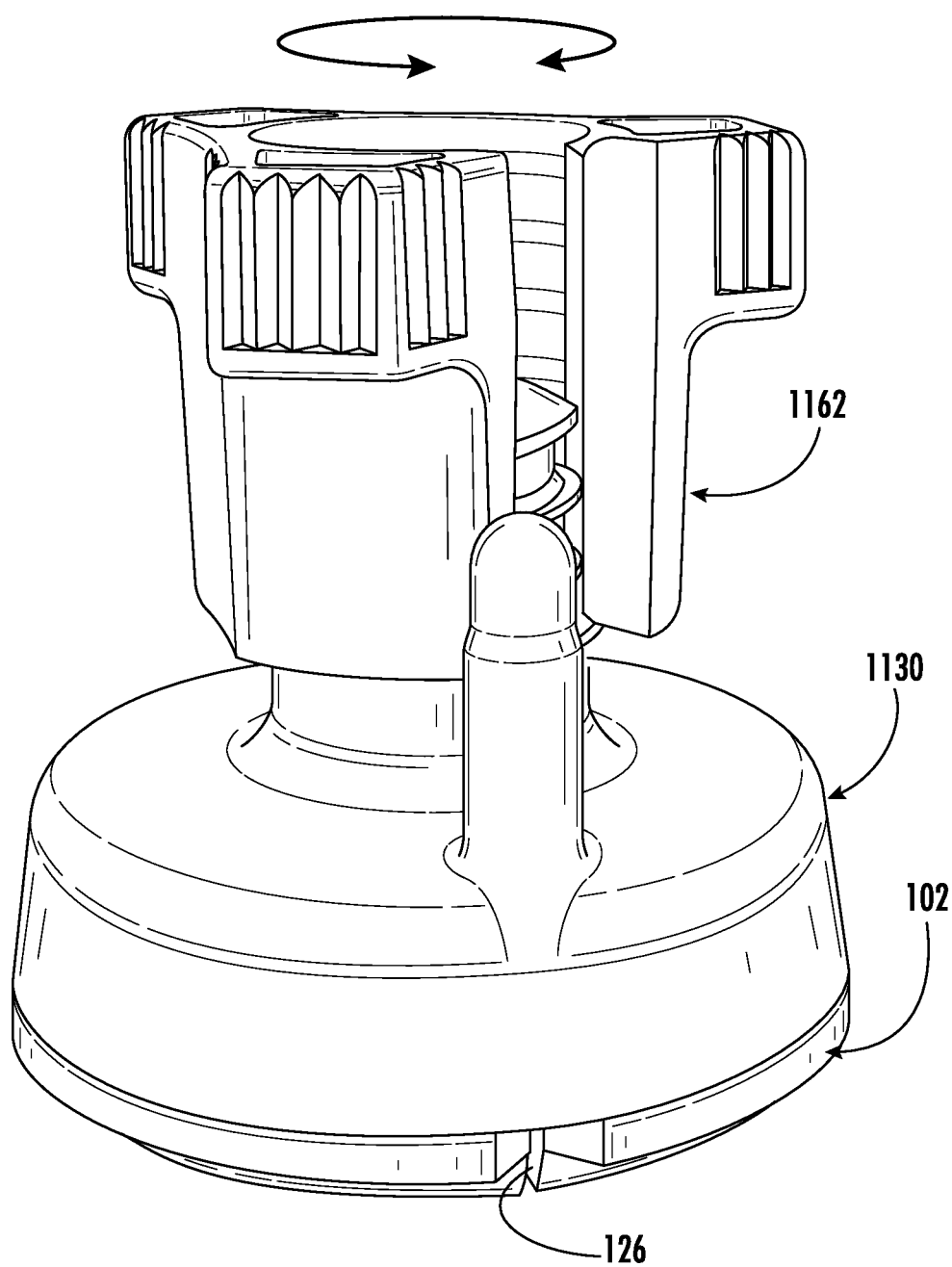
FIG. 18 presents an upper perspective view of the surgical pin compression wound dressing module and stabilizing device with the securing screw secured with the system in accordance with one aspect of the present embodiment of FIG. 14.

Referring to FIGS. 14 and 15, a surgical pin compression wound dressing stabilizing device 1130 is shown. The stabilizing device 1130 is configured to surround and allow adjustment along the surgical pin 202 in order to select a stationary position thereon at which to attach the stabilizing device to the surgical pin so as to thereby maintain or stabilize the surgical pin in an upright stationary orientation and concurrently compress and confine the wound dressing module 102 in a closed environment compressed again a patients skin. As seen in FIG. 17, the stabilizing device 1130 includes an upstanding body 1132 having an upright post 1134 and a bottom base 1136 being rigidly connected to one another such that the upright post 1134 is centrally disposed relative to and extends upwardly above the bottom base 1136.

More particularly, as seen in FIGS. 16, 17, 19 and 20, the upright post 1134 of the upstanding body 1132 has an annular wall 1138 defining a longitudinal passageway 1140 through the upstanding body that has a cross-sectional size generally the same as the cross-sectional size of the central orifice 124 through the main body 104 of the wound dressing module 102 such that both will slidably fit about the surgical pin 202. The bottom base 1136 of the upstanding body 1132 has an upper surface 1142 that tapers outwardly and downwardly from a lower end portion 1144 of the upright post 1134 of the upstanding body, terminating in a rounded peripheral portion 1146 on the bottom base. The bottom base 1136 of the upstanding body 1132 also has a lower outer annular surface 1148 that aligns with the top annular surface 118 of the peripheral rib 116 on the wound dressing module 102.

In one non-limiting embodiment, the annular wall 1138 is truncated conical such that the lower end portion 1144 is wider than the upper end portion 1143. In operation, the stabilizing screw 1162 deforms the annular wall to frictionally lock the stabilizing device 1130 against the surgical pin 202. As the stabilizing screw 1162 is rotatably advanced towards the bottom base 1136, the stabilizing screw 1162 causes the circumferential closure and/or flattening of the annular wall 1138 as the truncated conical annular wall 1138 is pushed inward as the screw is rotatably advanced towards the wider lower end portion 1144. As the screw is advanced from the upper end portion 1143 towards the lower end portion 1144, the stabilizing screw 1162 causes at least a portion and/or all of wider portions of the annular wall 1138 to deform inward toward the surgical screw 202.

In a non-limiting embodiment, elasticity of the stabilizing device 1130 and its annular wall 1138 allows and/or causes resumption of shape when the stabilizing screw 162 is rotatably backed from the annular wall 1138.

The bottom base 1136 of the upstanding body 1132 further has a lower inner annular surface 1150 and a lower intermediate annular surface 1152 extending between and interconnecting the lower outer and inner annular surfaces 1148, 1150. The lower inner annular surface 1150 is recessed into the bottom base 1136 relative to its lower outer annular surface 1148. The lower intermediate annular surface 1152 of the bottom base 1136 is arcuate in configuration. The lower inner and intermediate annular surfaces 1150, 1152 of the bottom base 1136 together define a central cavity 1154 that is open downwardly from the bottom base 1136 and recessed into the bottom base. The central cavity 1154 surrounds and communicates with the longitudinal passageway 1140 through the upright post 1134 of the upstanding body 1132. As seen in FIGS. 16, 17, 19 and 20, the lower outer, lower inner and lower intermediate annular surfaces 1148, 1150, 1152 of the bottom base 1136 align and are mateable with the upper side of the compressive wound dressing module 102, namely the top annular surface 118 of the peripheral rib 116 of the module, the upper surface 106 of the main body 104 of the module and the upper rounded edge 112 of the main body of the module.

Figure 16:
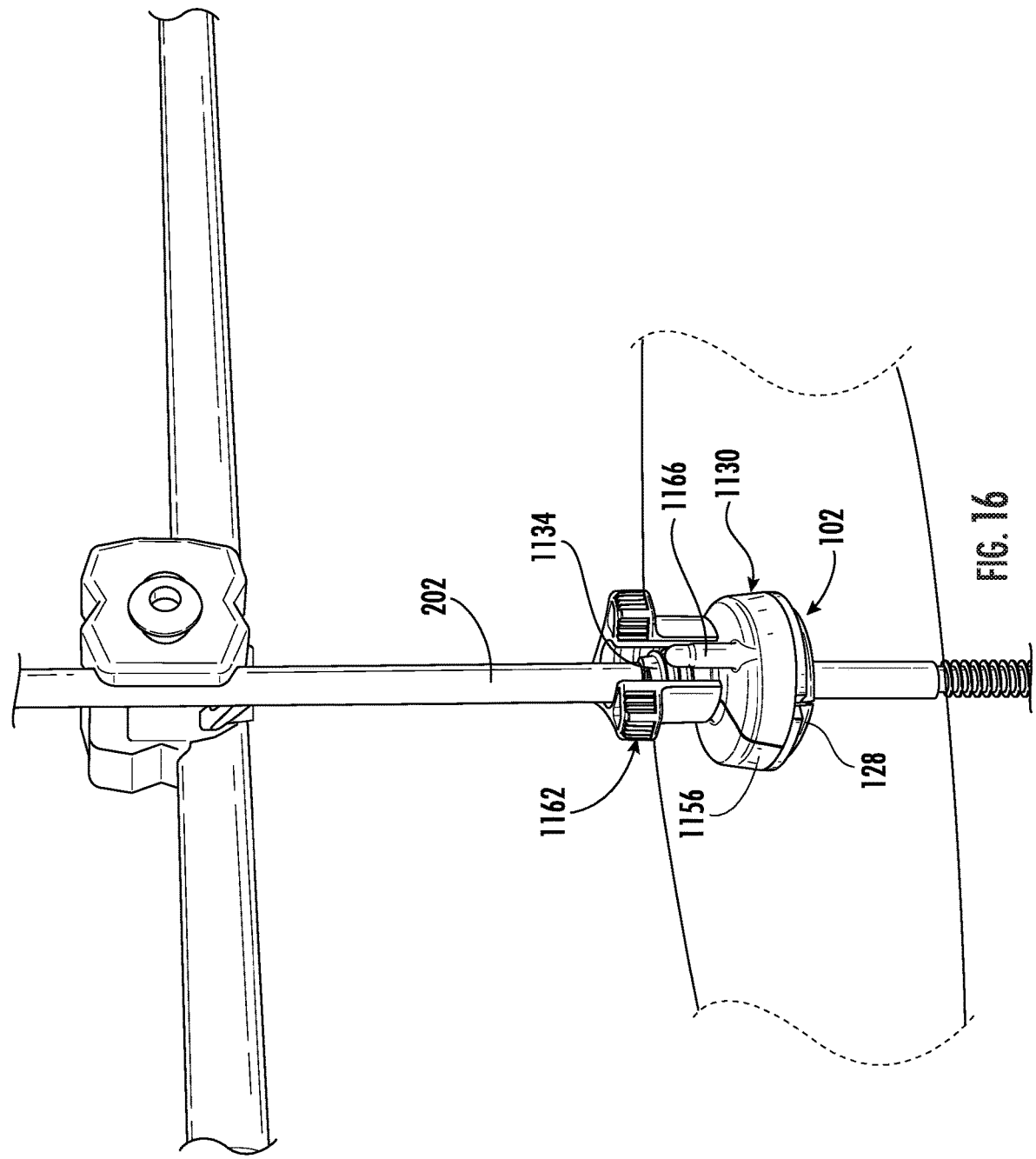
FIG. 16 presents an isometric view of the surgical pin compression wound dressing module and stabilizing device of the system positioned about a surgical pin in accordance with aspects of the present embodiment of FIG. 14.

In one non-limiting embodiment, the upright post 1134 and bottom base 1136 of the stabilizing device 1130 has a vertical slit 1156, which allows the stabilizing device to be capable of being disposed about the surgical pin 202 horizontally about the vertical slit 1156. The vertical slit 1156 separates the upstanding body 1132 and the bottom base 1136 to allow for a deformable opening when placing the stabilizing device 1130 about the surgical pin 202. The vertical slit 1156 allows the stabilizing device 1130 to temporarily deform to be placed about the surgical pin 202, as seen in FIGS. 15-16. The vertical slit 1156 of the stabilizing device 1130 also is optionally alignable with the radial slit 126 of the compressible wound dressing module 102. The vertical slit 1156 enables positioning of the upstanding body 1132 through the vertical slit and about the surgical pin 202 above the wound site 200 with the surgical pin disposed through the longitudinal passageway and central cavity.

In one non-limiting embodiment, the upright post 1134 and bottom base 1136 of the upstanding body 1132 of the stabilizing device 1130 does not have the vertical slit 1156, and instead such device is constructed and arranged to be capable of being cut to provide a substantially similar vertical slit 1156. Although this embodiment provides that the stabilizing device 1130 is capable of being cut to provide a substantially similar vertical slit 1156, a stabilizing device 1130 not capable of being cut is still within the spirit and scope of the present invention.

The upright post 1134 of the upstanding body 1132 of the stabilizing device 1130 has external threading 1160 along the upright post 1134. The external threading 1160 is designed to a receive rotatable stabilizing screw 1162. The stabilizing screw 1162 has internal threading 1164 and is constructed and arranged for threadingly engaging with the external threading 1160. The stabilizing screw 1162 is configured to rotate about the surgical pin 202. The stabilizing screw 1162 is constructed and arranged to rotate in one direct down about the upright post 1134 for locking the upstanding body 1132 in a position about the surgical pin 202. Due the annular configuration of its upstanding body 1132, the stabilizing device 1130 is able to apply an equal distribution of force upon the compressible wound dressing module 102 when a downward pressure is imposed on the stabilizing device when the stabilizing device 1130 rotatably receives the stabilizing screw 1162 about the upright post 1134. The stabilizing screw 1162 has a central vertical channel 1170.

In one non-limiting embodiment, the stabilizing screw 1162 includes a first vertical distal edge 1172 and a second vertical distal edge 1174. The first and second vertical distal edge 1172, 1174 are provided with a vertical gap therebetween such that the stabilizing screw 1162 can be placed on and/or removed from the surgical pin 202 (See FIGS. 15-16 for examples of the stabilizing screw 1162 on and off of the surgical pin 202).

In one non-limiting embodiment, the stabilizing screw 1162 is formed of rigid plastic such that the distance between the first and second distal edges 1172, 1174 will not increase or otherwise expand when placing the stabilizing screw 1162 on and off of the surgical pin. Subsequently, the stabilizing screw 1162 is rotatably coupled about the reciprocal threading of the stabilizing device 1130 for intending to lock the stabilizing device 1130 in place about the surgical pin 202, in accordance with the spirit and scope of the present invention.

In yet another non-limiting embodiment, the stabilizing screw 1162 may temporarily deform and open as the stabilizing screw 1162 is urged on the surgical pin 202, such that the distance between the first and second distal edges 1172, 1174 will increase in there distance therebetween to allow the central vertical channel 1170 to sit around the surgical pin. Subsequently, the stabilizing screw 1162 is rotatably coupled about the reciprocal threading of the stabilizing device 1130 for intending to lock the stabilizing device 1130 in place about the surgical pin 202, in accordance with the spirit and scope of the present invention.

Figure 19:
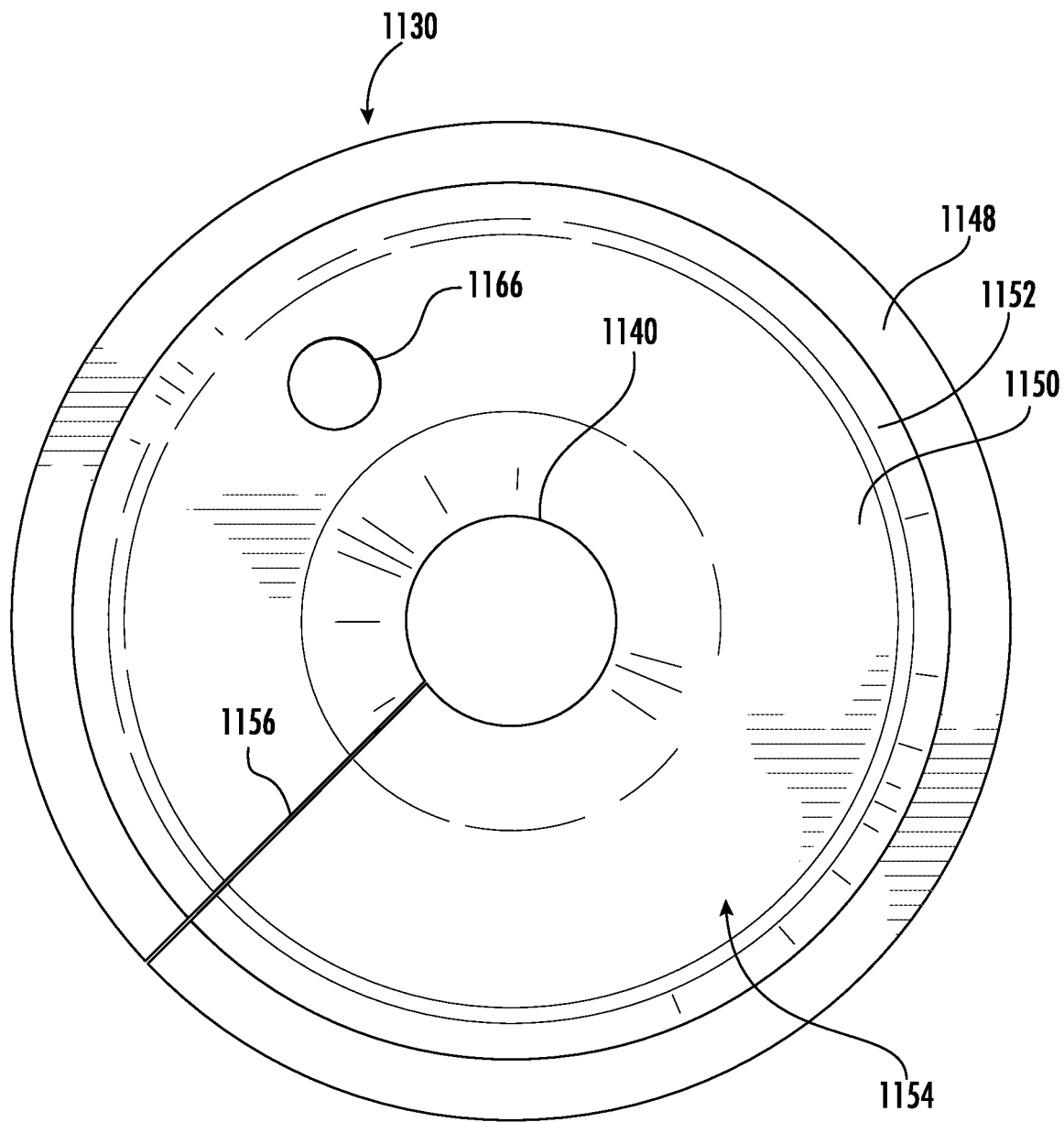
FIG. 19 presents a bottom view of the stabilizing device in accordance with one aspect of the present embodiment of FIG. 14.
Figure 20:
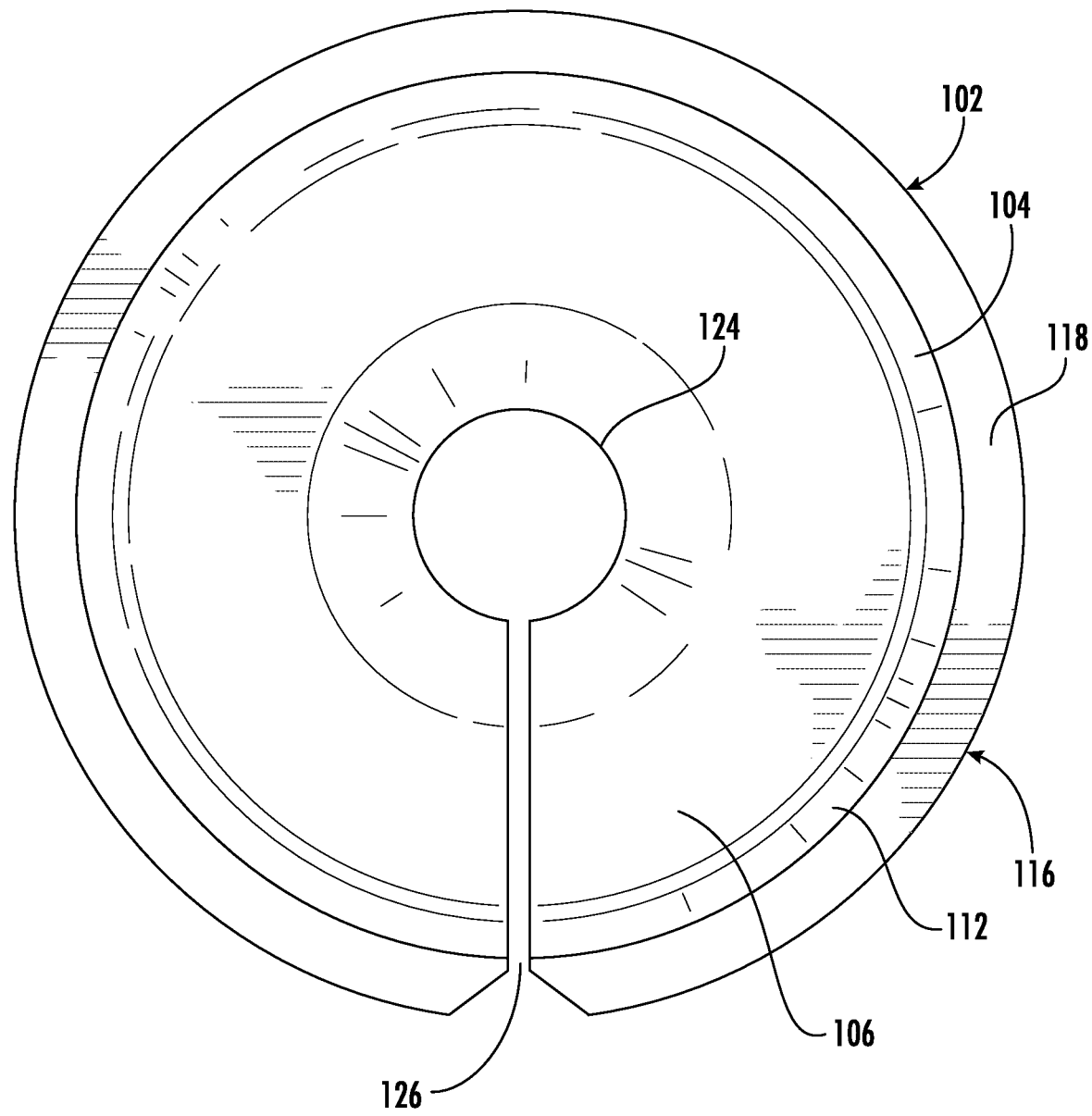
FIG. 20 presents a top view of the surgical pin compression wound dressing module in accordance with one aspect of the present embodiment.

As seen in FIGS. 17 and 19, the bottom base 1136 of the stabilizing device 1130 has a drainage port 1166 defined therein extending from the upper surface 1142 to the lower inner annular surface 1150 of the bottom base so as to provide communication from the compressive wound dressing module 102 in the central cavity 1154 of the bottom base to the exterior of the stabilizing device 1130 to thereby allow drainage from the central cavity 1154. An optional removal distal end 1168 is provided for removal if the drainage port is to be utilized. The drainage port 1166 may be a small diameter channel sized, shaped and otherwise configured for having a length of drainage tubing selectively attached thereto, such that the drainage tubing provides a communication pathway through bottom base 1136 of upstanding body 1132.

In one non-limiting embodiment, the distal end 1168 may be removed from the drainage port 1166 via tearing it off. In another non-limiting embodiment, the distal end 1168 requires removal via a mechanical tool, such as scissors, a knife, or other sharp mechanical tool, such that removal opens a channel about the drainage port 1166 for draining fluids.

Functionally, the stabilizing device 1130 isolates the surgical pin 202 and the surgical wound site 200 from potential contaminants originating from outside the wound site while also decreasing the amount of wound drainage. Furthermore, the stabilizing device 1130 allows for a precise geometrical coupling with the compressible wound dressing module 102. This quality gives the stabilizing device 1130 the potential to provide the desired compression of the wound dressing module 102.

In one non-limiting embodiment, the stabilizing device 1130 may be made from a plastic material capable of providing the device with pliable, structural characteristics. It would be advantageous to utilize a plastic material capable of withstanding conventional operating room sterilization techniques. Any and/or all conventional plastic molding process may be utilized to manufacture the stabilizing device 1130.

In a non-limiting embodiment, the stabilizing device 1130 is made from a non-rigid plastic material capable of deforming when being slipped on or slipped off the surgical pin 202, such that fresh new stabilizing device 1130 may be substituted about the surgical pin for hygiene purposes and preventing infections of a patient. Subsequent to slipping the stabilizing device disposed about a surgical pin 202, the user can apply a downward force to the stabilizing device 1130 in a direction toward the wound site 200, thereby engaging the lower outer annular surface 1148 of the bottom base 1136 of the stabilizing device 130 with the top annular surface 118 of the peripheral rib 116 of the wound dressing module 102. Preferably, this is accomplished in such a manner that the upper portion of the wound dressing module 102 is snugly received within central cavity 1154 of the bottom base. Downward compression of the module 102 brings the bottom annular surface 120 of the peripheral rib 116 into optional contact with the patient's skin at the wound site 200, with the bottom portion of the main body 104 of the module 102 pressing against the flesh of the patient surrounding the wound site. The peripheral rib 116 optionally acts as a buffer between the patient's skin and the stabilizing device 1130. The amount of applied downward pressure will directly determine the corresponding degree of wound compression exerted upon the wound site of the patient. Finally, when a desired degree of wound compression is achieved, the user can simply adjust the stabilizing screw 1162 to selectively secure the stabilizing device 1130 about the surgical pin 202. Wound dressing module changes are easily performed by the health care provider or the patient by repeating the process mentioned above.

The surgical pin compressive wound dressing stabilizing device 1130 is a biomedical mechanical device that allows for a compressive wound dressing to be applied and stabilized to the surgical pin sites of medical devices such as, for example, halos, external traction pins and other such devices that utilize surgical wires or pins. This medical device may be provided in any of a myriad of shapes, sized and configurations, without departing from the scope of the invention. However, the wound dressing module 102 is preferably provided having a geometry and size conforming to the central cavity 1154 in the underside of the bottom base 1136. Accordingly, the wound dressing modules 102 are preferably manufactured to custom fit corresponding pre-manufactured wound dressings. The closed environment provided by the wound dressing stabilizing device prevents wound drainage and helps prevent against bacterial contamination. Together the above-described components of the system 1000 provide a means for applying wound compression to the wound site 200 of a surgical pin 202 while also stabilizing the surgical pin 202. Structurally, the rigid nature of the stabilizing device 1130, as well as its precise fit as it couples with a specific wound dressing module, allows for symmetrical wound compression.

By providing a closed environment for the wound dressing material, the stabilizing device 1130 acts to isolate the wound dressing module and its corresponding wound drainage from the patient's adjacent skin. Furthermore, the system 1000 allows for surgical pin stability and also variability with regards to the amount of wound compression desired.

The easy use and effectiveness of the stabilization system 1000 enable medical staff to become more efficient and waste less time with laborious ineffective tasks such as time-consuming wound dressing changes. Consequently, more time could be used for other patients resulting in an increase in the quality of patient care. For patients wound dressing changes at home after discharge from hospitals with surgical pins in place would be quite easily managed. The easy handling and manipulating of the stabilization system 1000 allow all patients, even those lacking formal experience with post-surgical wound care methods, to properly care for their surgical wound sites. The decrease in both wound care supplies needed and medical waste generated, from the large quantity of discarded wound dressing bandages utilized, will ultimately cut health care costs.

Figure 21:
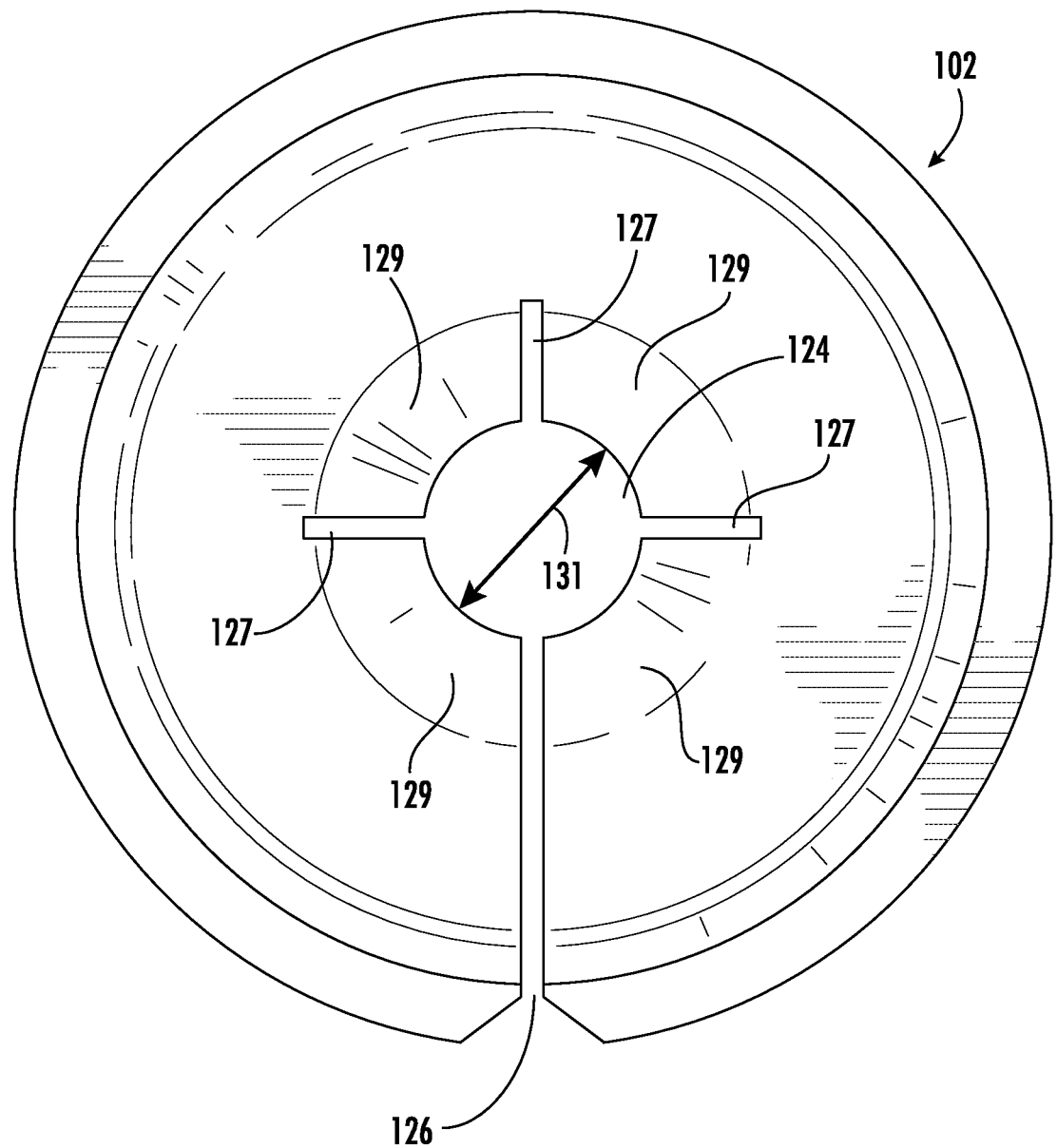
FIG. 21 presents a top view of an alternative embodiment of the surgical pin compression wound dressing module in accordance with one aspect of the present invention.

Referring to FIG. 21, a non-limiting alternative embodiment of the wound dressing module 102 is shown. The wound dressing module 102 includes the same radial slit 126 as provided throughout this invention, but this embodiment additionally provides additional partial radial slits 127 that accommodate various gauge and/or width of surgical pin 202 thickness. In operation, the partial radial slits 127 provide flexibility for placing the wound dressing module 102 about variously sized thickness of surgical pins 202. The partial slits 127 create central tabs 129 that can displace, including displacing in, up, or down when placed about a surgical pin 202 that has a width greater than the width 131 of the central orifice 124.

Figure 22:
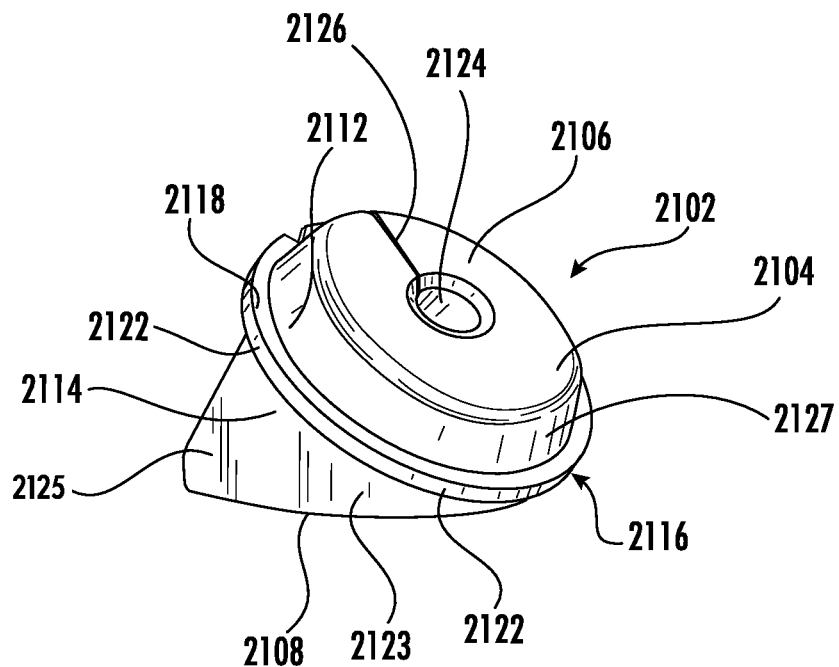
FIG. 22 presents a upper perspective view of an alternative embodiment of the wound dressing module in accordance with one aspect of the present embodiment.
Figure 23:
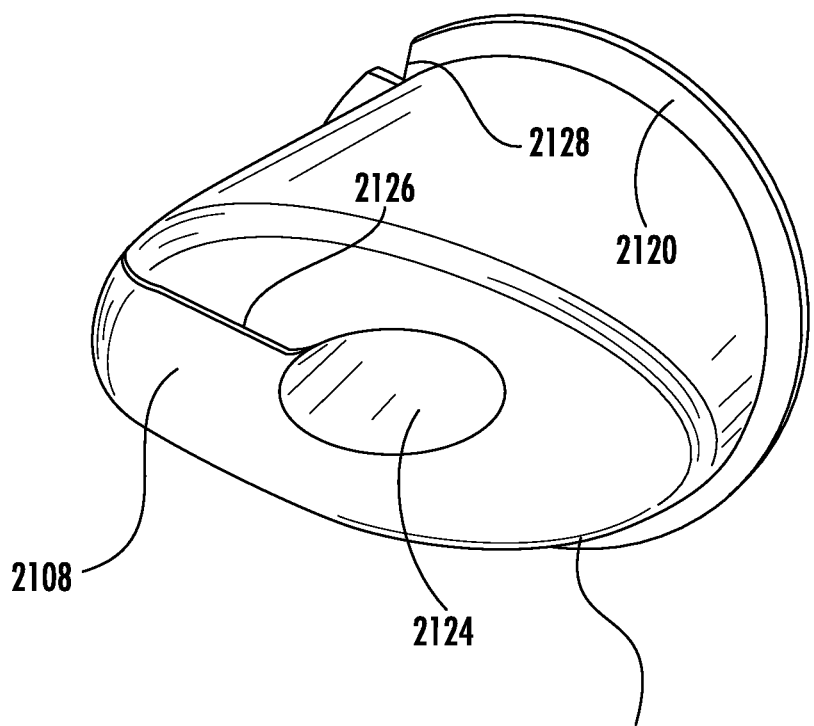
FIG. 23 presents a lower perspective view of an alternative embodiment of the wound dressing module in accordance with one aspect of the present embodiment of FIG. 22.
Figure 24:
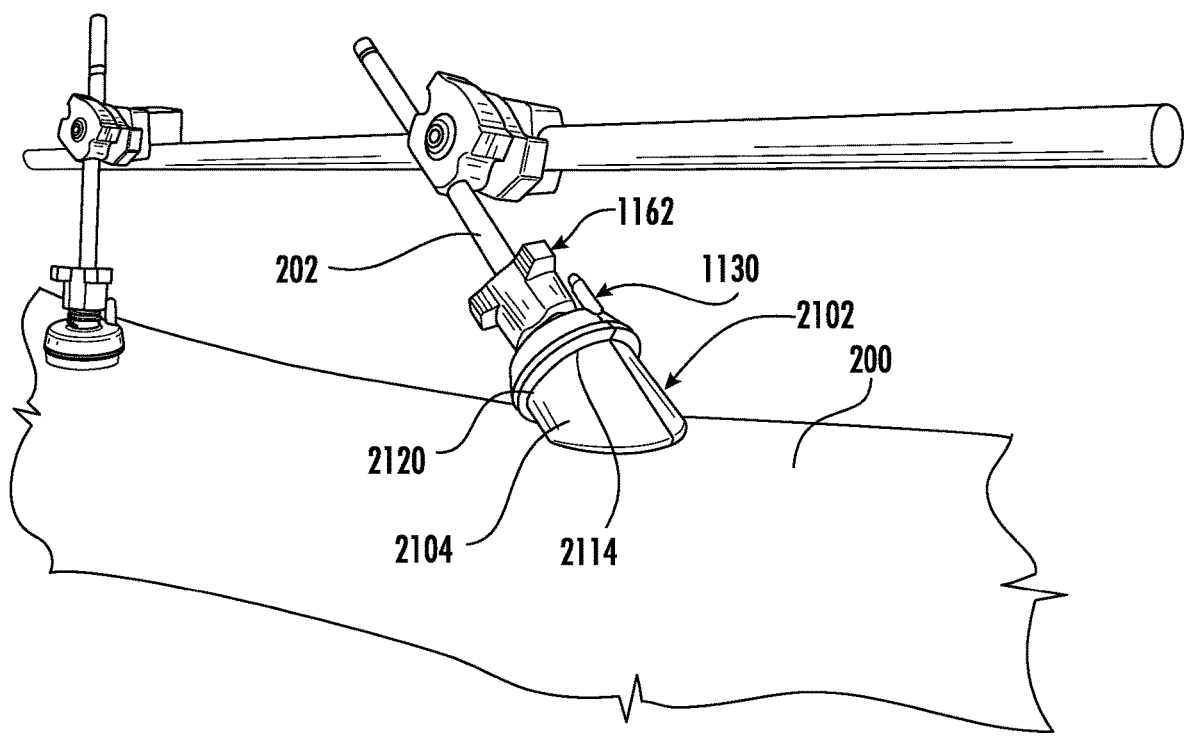
FIG. 24 presents an upper isometric view of the surgical pin compression wound dressing module of FIG. 22 and stabilizing device of the system stabilizing the wound dressing module of FIG. 14 and the surgical pin in accordance with aspects of the present embodiment.

Referring to FIGS. 22-24, a non-limiting alternative embodiment of the wound dressing module 102, the wound dressing module 2102 is shown. In this alternative embodiment, the wound dressing module 2102 is shaped such that the surgical pin can be placed at an angle, as shown in FIGS. 22-24. The wound dressing module 2102 has a main body 2104 composed of a compressive wound dressing, preferably in the form of a conventional sponge material having a predetermined configuration and size customized in accordance with the requirements of the patient's wound site 200 and the particular surgical pin 202 at the wound site. The main body 2104 of the module 2102 has upper and lower surfaces 2106, 2108.

Preferably, the wound dressing module 2102 has a peripheral rib 2116 integrally connected to the main body 2104. The peripheral rib 2116 is spaced from and located between the rounded upper and lower corners 2112, 2114 of the main body 2104. The peripheral rib 2116 has an annular configuration that protrudes from the main body 2104, and has top and bottom annular surfaces 2118, 2120 extending perpendicularly outward from the main body 2104, terminating at an outer circumferential surface 2122 of the peripheral rib. The peripheral rib 2116 may be composed of the same compressive wound dressing sponge material and may have the same predetermined configuration as the main body 2104.

Further, the wound dressing module 2102 may have a central orifice 2124 extending through main body 2104 between, and open at, the upper and lower surfaces 2106, 2108 thereof. The main body 2104 and peripheral rib 2116 of the module 2102 have a radial slit 2126 formed through and extending from an outer V-shaped entrance 2128, provided in the outer circumferential surface 2122 of the peripheral rib 2116, to the central orifice 2124 of the main body 2104. The radial slit 2126 in the module 2102 enables opening of the main body 2104 and peripheral rib 2116 of the module 2102 sufficiently to allow fitting of the module 2102 about the surgical pin 202 projecting above the wound site 200 with the surgical pin disposed through the central orifice 2124 of the main body. In an alternate implementation, lower surface 2108 of wound dressing module main body 2102 could incorporate a concave surface in lieu of the planar lower surface 2108 shown in the accompanying figures. Furthermore, it will be apparent to those skilled in the art that rounded corners 2112 and 2114 could be provided squared off, beveled or incorporating any other surface geometry consistent with the operation of the invention.

The planar lower surface 2108 of the wound dressing module 2102 is inclined cropped through the module 2102 creating a wedge such that the wound dressing module body 2123 has a thick end portion 2125 and tapering to a thin end portion 2127.

It will be apparent to those skilled in the art that the wound dressing module 2102 is constructed and arranged to couple with either of the wound stabilizing device 130, 1130 in substantially the same manner and method of the wound dressing module 102 described herein, only changing the orientation of the device in relation to the wound. The would dressing module 2102 is constructed and arranged to compress a wound about a surgical pin 202 at a desired angle.

It is within the spirit and scope of this embodiment that different shapes for the wound dressing module 102 and 2102 may be provided such that this system can be implemented with various angles and positionings of the surgical pin.

What is claimed is:

1. A surgical pin compressive wound dressing stabilizing device, comprising: an upstanding body comprising:

an upright post having an annular wall defining a longitudinal passageway through said upright post being open at opposite ends of said longitudinal passageway, and a bottom base connected to and extending outwardly from a lower portion of said upright post such that said upright post is centrally disposed relative to and extends upwardly above said bottom base, said bottom base defining a central cavity open at a bottom of said upstanding body that surrounds and communicates with said longitudinal passageway of said upright post and is recessed into said bottom base for mating with an upper portion of a compressive wound dressing module receivable into said central cavity;

a securement member engaging said upright post; and wherein said securement member secures said upstanding body about a surgical pin via said securement member to impart downward compression against said compressive wound dressing module.

2. The surgical pin compressive wound dressing stabilizing device according to claim 1 wherein said upright post and said bottom base have a vertical slit to enable the stabilizing device constructed and arranged to deform said upstanding body to be placed about a surgical pin projecting above a wound site with the surgical pin disposed through said longitudinal passageway and central cavity.

3. The surgical pin compressive wound dressing stabilizing device according to claim 1 wherein said bottom base also defines a lower outer annular surface surrounding said central cavity for engaging a peripheral rib on the compressive wound dressing module to enable application of an equal distribution of a downward compressive pressure by said upstanding body upon the compressive wound dressing module.

4. The surgical pin compressive wound dressing stabilizing device of claim 1 wherein said upright post further having a first reciprocating threading.

5. The surgical pin compressive wound dressing stabilizing device according to claim 4 further comprising a stabilizing screw with a second reciprocating threading, wherein said stabilizing screw is rotatably securable with said upright post about first and second reciprocating threading for securing said upstanding body at a desired location along the surgical pin.

6. The surgical pin compressive wound dressing stabilizing device according to claim 5, wherein said stabilizing screw further includes a first distal edge and a second distal edge with an associated vertical gap therebetween for providing a space for urging the stabilizing screw about the surgical pin.

7. The surgical pin compressive wound dressing stabilizing device according to claim 1, further comprising a drainage port on said bottom base in communication with said central cavity of said bottom base to optionally allow drainage from a wound site through said central cavity.

8. The surgical pin compressive wound dressing stabilizing device according to claim 7, further comprising a removable distal end that is removable for opening said drainage port.

9. The surgical pin compressive wound dressing stabilizing device according to claim 8 wherein said removable distal end is permanently removed when removed for opening said drainage port.

10. The surgical pin compressive wound dressing stabilizing device according to claim 1 wherein said central cavity of said bottom base is defined by a lower inner annular surface and a lower intermediate annular surface extending between and interconnecting a lower outer annular surface, said lower inner annular surface being recessed into said bottom base relative to an outer annular surface.

11. The surgical pin compressive wound dressing stabilizing device according to claim 10 wherein said lower intermediate annular surface is arcuate in configuration.

12. A surgical pin compressive wound dressing module, comprising:

a main body composed of a compressive wound dressing, said main body having upper and lower surfaces spaced apart and extending substantially non-parallel to one another and an outer circumferential surface extending between and merging with said upper and lower surfaces so as to form upper and lower corners of said main body, said main body also having a central orifice formed therethrough between and open at said upper and lower surfaces thereof; and a peripheral rib connected to, extending about and protruding radially outward from said outer circumferential surface of said main body, said peripheral rib being spaced from and located between said upper and lower corners of said main body and having top and bottom annular surfaces extending perpendicularly outward from said outer circumferential surface of said main body and terminating at an outer circumferential surface of said peripheral rib; and wherein said main body and peripheral rib have a radial slit therethrough from said outer circumferential surface of said peripheral rib to said central orifice of said main body to enable opening of said main body and peripheral rib and fitting of said module about a surgical pin projecting above a wound site with the surgical pin disposed through said central orifice of said main body.

13. The surgical pin compressive wound dressing module according to claim 12 wherein said main body of said module is composed of a compressive wound dressing made of a sponge material.

14. The surgical pin compressive wound dressing module according to claim 12 wherein said peripheral rib is composed of the said compressive wound dressing.

15. The surgical pin compressive wound dressing module according to claim 12 wherein said peripheral rib defines an outer V-shaped entrance formed in said outer circumferential surface from which said radial slit extends into said peripheral rib.

16. A surgical pin compressive wound dressing stabilizing system, comprising:

a surgical pin compressive wound dressing module comprising:

a main body composed of a compressive wound dressing, said main body having upper and lower surfaces spaced apart and extending generally parallel to one another and an outer circumferential surface extending between and merging with said upper and lower surfaces so as to form upper and lower corners of said main body, said main body also having a central orifice formed therethrough between and open at said lower and upper surfaces thereof; and a peripheral rib connected to, extending about and protruding radially outward from said outer circumferential surface of said main body, said peripheral rib being spaced from and located between said upper and lower corners of said main body and having top and bottom annular surfaces extending perpendicularly outward from said outer circumferential surface of said central body and terminating at an outer circumferential surface of said peripheral rib; and wherein said main body and peripheral rib have a radial slit therethrough from said outer circumferential surface of said peripheral rib to said central orifice of said main body to enable opening of said main body and peripheral rib and fitting said module about a surgical pin projecting above a wound site with the surgical pin disposed through said central orifice of said main body; and a surgical pin compressive wound dressing stabilizing device comprising:

an upstanding body comprising:

an upright post having an annular wall defining a longitudinal passageway through said upright post being open at opposite ends of said longitudinal passageway; and a bottom base connected to and tapering outwardly and downwardly from a lower portion of said upright post such that said upright post is centrally disposed relative to and extends upwardly above said bottom base, said bottom base defining a central cavity open at a bottom of said upstanding body that surrounds and communicates with said longitudinal passageway of said upright post and is recessed into said bottom base for mating with an upper portion of said compressive wound dressing module above said top annular surface of said peripheral rim of said compressive wound dressing module, wherein said upright post and said bottom base have a vertical slit to enable said upstanding body entry about, and removal from, the surgical pin projecting above a wound site with the surgical pin disposed through said longitudinal passageway and central cavity; and wherein said bottom base also defines a lower outer annular surface surrounding said central cavity for engaging said peripheral rib on said compressive wound dressing module to enable application of an equal distribution of a downward compressive pressure by said upstanding body upon said compressive wound dressing module; and a stabilizing screw that rotatably secures about an outer surface of said upright post of said upstanding body for securing said upstanding body at a desired location along the surgical pin.

17. The surgical pin compressive wound dressing stabilizing system according to claim 16 further comprising a drainage port on said bottom base in communication with said central cavity of said bottom base to allow drainage from the wound site through said central cavity.

18. The surgical pin compressive wound dressing stabilizing system according to claim 17 wherein said drainage port includes a permanently removable distal end creating a distal opening in the drainage port when said permanently removal distal end is removed from said drainage port.

19. The surgical pin compressive wound dressing stabilizing system according to claim 16 wherein said main body of said module is composed of a compressive wound dressing made of a sponge material.

20. The surgical pin compressive wound dressing stabilizing system according to claim 16 wherein said peripheral rib is composed of said compressive wound dressing.

* * * * *